US012691045B2

(12) United States Patent
Lynch et al.

(10) Patent No.: US 12,691,045 B2
(45) Date of Patent: *Jul. 28, 2026

(54) RHEOLOGICAL SOLID COMPOSITION FOR USE IN SHAVING

(71) Applicant: The Procter & Gamble Company, Cincinnati, OH (US)

(72) Inventors: Matthew Lawrence Lynch, Mariemont, OH (US); Brandon Philip Illie, Felicity, OH (US); Taotao Zhu, West Chester, OH (US); Jamie Lynn Dria, Deerfield Township, OH (US); Paul Martin Lipic, West Chester, OH (US); Valerie Jean Bradford, Framingham, MA (US); Alison Stephens, Cookham Maidenhead (GB); Philip Andrew Sawin, Wyoming, OH (US)

(73) Assignee: The Procter & Gamble Company, Cincinnati, OH (US)

(*) Notice: Subject to any disclaimer, the term of this patent is extended or adjusted under 35 U.S.C. 154(b) by 159 days.

This patent is subject to a terminal disclaimer.

(21) Appl. No.: 17/225,151

(22) Filed: Apr. 8, 2021

(65) Prior Publication Data

US 2021/0322290 A1 Oct. 21, 2021

Related U.S. Application Data

(60) Provisional application No. 63/007,972, filed on Apr. 10, 2020.

(51) Int. Cl.

| | |
|---|---|
| ***A61K 8/36*** | (2006.01) |
| ***A61K 8/02*** | (2006.01) |
| ***A61K 8/04*** | (2006.01) |
| ***A61K 8/06*** | (2006.01) |
| ***A61K 8/19*** | (2006.01) |
| ***A61K 8/20*** | (2006.01) |
| ***A61K 8/34*** | (2006.01) |
| ***A61K 8/73*** | (2006.01) |
| ***A61K 8/92*** | (2006.01) |
| ***A61Q 9/02*** | (2006.01) |

(52) U.S. Cl.

CPC ............ *A61K 8/361* (2013.01); *A61K 8/0216* (2013.01); *A61K 8/044* (2013.01); *A61K 8/06* (2013.01); *A61K 8/19* (2013.01); *A61K 8/20* (2013.01); *A61K 8/34* (2013.01); *A61K 8/73* (2013.01); *A61K 8/92* (2013.01); *A61Q 9/02* (2013.01); *A61K 2800/48* (2013.01); *A61K 2800/524* (2013.01)

(58) Field of Classification Search

CPC . A61K 8/19; A61K 8/06; A61K 8/922; A61K 8/027; A61K 8/361; A61K 8/34; A61K 8/345; A61K 8/044; A61K 8/20; A61K 8/73; A61K 8/92; A61K 8/0216; A61K 2800/524; A61K 2800/48; A61Q 9/02; A61Q 19/10

See application file for complete search history.

(56) References Cited

U.S. PATENT DOCUMENTS

| | | | | | |
|---|---|---|---|---|---|
| 823,725 | A | | 6/1906 | Hayden | |
| 3,112,219 | A | | 11/1963 | Alfred | |
| 3,293,684 | A | | 12/1966 | Otto | |
| 3,585,144 | A | | 6/1971 | Schiltz | |
| 3,810,841 | A | | 5/1974 | Richter | |
| 3,956,158 | A | | 5/1976 | Donaldson | |
| 4,107,289 | A | | 8/1978 | Kaufman | |
| 4,203,857 | A | | 5/1980 | Dugan | |
| 4,322,400 | A | | 3/1982 | Yuhas | |
| 4,486,404 | A | | 12/1984 | Weinert | |
| 4,806,340 | A | | 2/1989 | Gaffar | |
| 4,808,467 | A | | 2/1989 | Suskind et al. | |
| 5,144,729 | A | | 9/1992 | Austin et al. | |
| 5,160,739 | A | * | 11/1992 | Kanga | A61K 8/39 514/939 |
| 5,340,492 | A | | 8/1994 | Kacher et al. | |
| 5,340,571 | A | * | 8/1994 | Grace | A61K 8/44 424/73 |
| 5,425,892 | A | | 6/1995 | Taneri et al. | |
| 5,436,278 | A | | 7/1995 | Imashiro et al. | |
| 5,525,397 | A | | 6/1996 | Shizuno et al. | |
| 5,585,092 | A | | 12/1996 | Trandai et al. | |
| 5,605,681 | A | | 2/1997 | Trandai et al. | |
| 5,691,035 | A | | 11/1997 | Chappell et al. | |
| 5,846,520 | A | | 12/1998 | Guskey et al. | |
| 5,916,590 | A | | 6/1999 | Cody et al. | |
| 6,042,815 | A | | 3/2000 | Kellner et al. | |
| 6,143,393 | A | | 11/2000 | Abe et al. | |

(Continued)

FOREIGN PATENT DOCUMENTS

| | | | |
|---|---|---|---|
| CA | 680113 | A | 2/1964 |
| CN | 107440935 | A | 12/2017 |

(Continued)

OTHER PUBLICATIONS

PCT Search Report and Written Opinion for PCT/US2021/026294 dated Jul. 16, 2021.
All Office Actions, U.S. Appl. No. 17/196,379.
All Office Actions, U.S. Appl. No. 17/225,146.
All Office Actions, U.S. Appl. No. 17/225,148.
All Office Actions, U.S. Appl. No. 17/225,149.
All Office Actions, U.S. Appl. No. 17/225,150.
All Office Actions, U.S. Appl. No. 17/225,153.
All Office Actions, U.S. Appl. No. 17/225,176.
All Office Actions, U.S. Appl. No. 17/225,218.
Clinton D. Stevenson, et al. ,"Capillary Pressure as Related to Water Holding in Polyacrylamide and Chicken Protein Gels", Journal of Food Science, vol. 78, Nr. 2, dated 2013,pp. C145-C151.

(Continued)

*Primary Examiner* — Lezah Roberts

(74) *Attorney, Agent, or Firm* — Kathleen Y. Carter; James E. Oehlenschlager

(57) ABSTRACT

A rheological solid shave composition. The rheological solid shave composition has a crystallizing agent, an active and an aqueous phase.

8 Claims, 8 Drawing Sheets

(56) References Cited

U.S. PATENT DOCUMENTS

| | | | |
|---|---|---|---|
| 6,241,835 B1 | 6/2001 | Abe et al. | |
| 6,245,413 B1 | 6/2001 | Kenmochi et al. | |
| 6,329,308 B1 | 12/2001 | Kenmochi et al. | |
| 6,550,092 B1 | 4/2003 | Brown et al. | |
| 6,554,937 B1 | 4/2003 | Kenmochi et al. | |
| 6,774,070 B1 | 8/2004 | Kenmochi et al. | |
| 6,777,064 B1 | 8/2004 | Brown et al. | |
| 6,797,357 B2 | 9/2004 | Fereshtehkhou et al. | |
| 6,813,801 B2 | 11/2004 | Tanaka et al. | |
| 6,936,330 B2 | 8/2005 | Fereshtehkhou et al. | |
| 7,003,856 B2 | 2/2006 | Hayashi et al. | |
| 7,041,277 B2 | 5/2006 | Holme | |
| 7,291,359 B2 | 11/2007 | Haskett et al. | |
| 7,386,907 B2 | 6/2008 | Otsuka et al. | |
| 7,560,398 B2 | 7/2009 | Zillig et al. | |
| 7,566,671 B2 | 7/2009 | Hoadley et al. | |
| 7,712,178 B2 | 5/2010 | Yamada | |
| 7,779,502 B2 | 8/2010 | Fujiwara et al. | |
| 7,937,797 B2 | 5/2011 | Tsuchiya et al. | |
| 8,075,977 B2 | 12/2011 | Curro et al. | |
| 8,093,192 B2 | 1/2012 | Liu et al. | |
| 8,146,197 B2 | 4/2012 | Yamada | |
| 8,151,402 B2 | 4/2012 | Takabayashi et al. | |
| 8,161,594 B2 | 4/2012 | Policicchio et al. | |
| 8,186,001 B2 | 5/2012 | Tsuchiya et al. | |
| 8,225,453 B2 | 7/2012 | Yamada | |
| 8,245,349 B2 | 8/2012 | Tsuchiya et al. | |
| 8,435,625 B2 | 5/2013 | Ruehe et al. | |
| 8,528,151 B2 | 9/2013 | Przepasniak | |
| 8,536,074 B2 | 9/2013 | Fereshtehkhou et al. | |
| 8,617,685 B2 | 12/2013 | Yamada | |
| 8,646,144 B2 | 2/2014 | Wada et al. | |
| 8,752,232 B2 | 6/2014 | Otsuka et al. | |
| 8,756,746 B2 | 6/2014 | Policicchio | |
| 8,763,197 B2 | 7/2014 | Policicchio et al. | |
| 8,793,832 B2 | 8/2014 | Yamada | |
| 8,851,776 B2 | 10/2014 | Schwarz et al. | |
| 8,858,971 B2 | 10/2014 | Rao | |
| 9,113,768 B2 | 8/2015 | Wada et al. | |
| 9,198,553 B2 | 12/2015 | Policicchio | |
| 9,204,775 B2 | 12/2015 | Pung et al. | |
| 9,296,176 B2 | 3/2016 | Escaffre et al. | |
| 9,339,165 B2 | 5/2016 | Vetter et al. | |
| 9,622,943 B2 | 4/2017 | Scala et al. | |
| 9,737,609 B2 * | 8/2017 | Vu | A61K 9/0095 |
| 10,076,583 B2 | 9/2018 | Lynch | |
| 10,143,764 B2 | 12/2018 | Lynch | |
| 10,821,056 B2 | 11/2020 | Swartz et al. | |
| 10,835,455 B2 | 11/2020 | Payne et al. | |
| 10,932,996 B2 | 3/2021 | Baig et al. | |
| 11,812,909 B2 | 11/2023 | Lynch | |
| 2001/0048933 A1 | 12/2001 | L'Alloret | |
| 2002/0160088 A1 | 10/2002 | Sakaguchi et al. | |
| 2003/0021760 A1 | 1/2003 | Kumar et al. | |
| 2003/0053980 A1 | 3/2003 | Dodd et al. | |
| 2004/0185011 A1 | 9/2004 | Alexander | |
| 2005/0152851 A1 | 7/2005 | Kaminski | |
| 2006/0024245 A1 | 2/2006 | Gebreselassie et al. | |
| 2009/0155190 A1 | 6/2009 | Gebreselassie et al. | |
| 2010/0061941 A1 | 3/2010 | Gebreselassie | |
| 2011/0027328 A1 | 2/2011 | Baig et al. | |
| 2011/0053826 A1 | 3/2011 | Wise | |
| 2011/0262507 A1 | 10/2011 | Spring | |
| 2013/0111682 A1 | 5/2013 | Pung | |
| 2013/0302385 A1 | 11/2013 | Muenz et al. | |
| 2014/0289984 A1 | 10/2014 | Vetter | |
| 2015/0196185 A1 | 7/2015 | Fiske | |
| 2015/0313803 A1 | 11/2015 | Lynch et al. | |
| 2015/0313808 A1 | 11/2015 | Lynch et al. | |
| 2016/0051684 A1 | 2/2016 | Wang | |
| 2016/0120771 A1 | 5/2016 | Simonet et al. | |
| 2016/0346175 A1 | 12/2016 | Sasik et al. | |
| 2018/0127692 A1 | 5/2018 | Coope-epstein et al. | |
| 2019/0160022 A1 | 5/2019 | Chiou | |
| 2019/0298625 A1 | 10/2019 | Hilliard, Jr. et al. | |
| 2019/0343732 A1 | 11/2019 | Mao | |
| 2020/0000693 A1 | 1/2020 | Traynor et al. | |
| 2021/0007940 A1 | 1/2021 | Swartz et al. | |

FOREIGN PATENT DOCUMENTS

| | | | | |
|---|---|---|---|---|
| DE | 202007001353 U1 | | 5/2007 | |
| EP | 0916722 A2 | | 5/1999 | |
| EP | 2465487 A2 | | 6/2012 | |
| EP | 2170257 B1 | | 11/2012 | |
| ES | 2548699 T3 | * | 10/2015 | A61K 8/042 |
| GB | 2221389 A | | 2/1990 | |
| WO | 9209679 A1 | | 6/1992 | |
| WO | 0196461 A1 | | 12/2001 | |
| WO | WO 02/087519 | * | 11/2002 | |
| WO | 03075735 A1 | | 9/2003 | |
| WO | 2007133265 A2 | | 11/2007 | |
| WO | 2009095891 A1 | | 8/2009 | |
| WO | 2010060653 A2 | | 6/2010 | |
| WO | 2014124066 A1 | | 8/2014 | |

OTHER PUBLICATIONS

F. V. Ryer, 0il & Soap, "Research Laboratory, Lever Brothers Company Cambridge, Massachusetts", dated Oct. 1946, pp. 310-313.

F. V. Ryer, et al. Growing Single Crystals, "A Method of Growing Single Crystals of Sodium Stearate and Sodium Palmitate", dated Feb. 4, 1944, pp. 154-158.

Marc N. G. de Mul, et al. Langmuir 2000, "Solution Phase Behavior and Solid Phase Structure of Long-Chain Sodium Soap Mixtures", vol. 16, No. 22, dated 2000, pp. 8276-8284.

Masao Sambuichi, et al. Dewatering of Gels, "Filtration, Food Chemical Engineering, Solid Liquid Separation, Dewatering, Expression, Gel", Journal of Chemical Engineering of Japan, vol. 27, No. 5, dated 1994, pp. 616-620.

Matthew L Lynch, Acid-soaps, "The study of acid-soap crystals has resulted in many conflicting data", Current Opinion in Colloid & Interface Science, dated 1997,pp. 495-500.

Matthew L. Lynch, et al. Acid-soap crystals, "Spectroscopic and Thermal Characterization of 1:2 Sodium Soap/Fatty Acid Acid-Soap Crystals", J. Phys. Chem., vol. 100, No. 1, 1996, pp. 357-361.

Matthew L. Lynch, Structure of Fatty Acid-Soap Crystals,"Intermolecular Interactions and the Structure of Fatty Acid-Soap Crystals", J. Phys. Chem. B, vol. 105, No. 2, dated 2001, pp. 552-561.

Theodore P. Labuza, et al. , "Measurement of Gel Water-Binding Capacity by Capillary Suction Potential", Journal of Food Science, vol. 43, dated 1978 ,pp. 1264-1269.

Unpublished U.S. Appl. No. 17/196,379, filed Mar. 9, 2021, to first inventor Geoffrey Marc Wise.

Unpublished U.S. Appl. No. 17/225,150, filed Apr. 8, 2021, to first inventor Matthew Lawrence Lynch et al.

Unpublished U.S. Appl. No. 17/225,218, filed Apr. 8, 2021, to first inventor Matthew Lawrence Lynch et al.

Unpublished U.S. Appl. No. 17/225,147, filed Apr. 8, 2021, to first inventor Matthew Lawrence Lynch et al.

Unpublished U.S. Appl. No. 17/225,149, filed Apr. 8, 2021, to first inventor Matthew Lawrence Lynch et al.

Unpublished U.S. Appl. No. 17/225,153, filed Apr. 8, 2021, to first inventor Matthew Lawrence Lynch et al.

Unpublished U.S. Appl. No. 17/225,176, filed Apr. 8, 2021, to first inventor Matthew Lawrence Lynch et al.

Unpublished U.S. Appl. No. 17/225,148, filed Apr. 8, 2021, to first inventor Matthew Lawrence Lynch et al.

All Office Actions; U.S. Appl. No. 17/485,906, filed Sep. 27, 2021.

Unpublished U.S. Appl. No. 17/485,906, filed Sep. 27, 2021, to first inventor et al.

All Office Actions; U.S. Appl. No. 18/450,176, filed Aug. 15, 2023.

Unpublished U.S. Appl. No. 18/450,176, filed Aug. 15, 2023, to Matthew Lawrence Lynch et al.

All Office Actions; U.S. Appl. No. 18/909,337, filed Oct. 8, 2024.

All Office Actions; U.S. Appl. No. 18/909,342, filed Oct. 8, 2024.

(56) References Cited

OTHER PUBLICATIONS

Unpublished U.S. Appl. No. 18/909,337, filed Oct. 8, 2024, Matthew Lawrence Lynch et al.
Unpublished U.S. Appl. No. 18/909,342, filed Oct. 8, 2024, Matthew Lawrence Lynch et al.
Robert B Saper et al.,"An Essential Micronutrient", vol. 79, No. 9, dated May 1, 2009, pp. 768-772.

* cited by examiner

RHEOLOGICAL SOLID COMPOSITION FOR USE IN SHAVING

FIELD OF THE INVENTION

Rheological solid composition comprising more than about 80% water having a crystallizing agent with an elongated, fiber-like crystal habit. Wherein the rheological solid composition allows for a unique skin feel "crunch" and/or glide when rubbed on the skin providing an enhanced evaporative cooling for a refreshing/cooling sensation, even in the absence of sensate; and wherein the rheological solid also exhibits properties of sufficient firmness, aqueous phase expression and thermal stability critical for practical commercial viability.

BACKGROUND OF THE INVENTION

Conventional high-water containing compositions, such as rheological solid compositions, lack one or more desirable properties, for example sufficient firmness, aqueous phase expression and thermal stability, particularly those comprising sodium carboxylate-based crystallizing agents. For instance, to produce a firm rheological solid composition using sodium stearate (C18) as a gelling agent in conventional soap-type deodorant gel-sticks requires the inclusion of high levels of polyols (e.g. propylene glycol and glycerin), as a solubility aid for the sodium stearate during processing, even at high process temperatures. Typical compositions include about 50% propylene glycol, 25% glycerin and only 25% water (EP2170257 and EP2465487). However, the addition of these processing aids eliminates the crunch and mutes the glide feel and cooling sensation of the solid gel stick. For a second example, traditional soap bars are comprised of similar gelling agents, but are far too concentrated in sodium carboxylate to effectively allow for aqueous phase expression with compression. Another example is where thermal stability is compromised in compositions by adding a too soluble gelling agent, as in (Kacher et al., U.S. Pat. No. 5,340,492). Specifically, the thermal stability temperature of the composition is too low to effectively survive reliably on the shelf life or in the supply chain.

Shaving—or the removal of hair over parts of the body, is a daily ritual for many consumers in which they undergo a series of the steps: hydrating skin (often with copious amount of water), applying lubricant in the form of foam or gel, running razor over skin to remove hair, rinsing off excess lubricant; wiping skin dry, applying skin treatment agent (such as after-shave), and applying fragrance and/or oils. Shaving or the removal of hair can include numerous devices such as wet razors, dry shavers, depilators, and intense pulsed light devices. This regimen often requires many products and resources, such as copious amounts of water; which places undue burdens in both time and expense on consumers. As an example, there are many places consumers do not have access to sufficient water to completely hydrate the skin. As other examples, consumers may not have access to all the products in a shaving or personal care regimen and therefore are not able to produce a desired outcome. Consumers need a consumer product that combines these separate steps to simplify the regimen and which includes all the resources for a complete shave.

What is needed is a rheological solid composition that has sufficient firmness, aqueous phase expression and thermal stability. The present invention of a self-supporting structure comprising a crystalline mesh of a relatively rigid, frame of fiber-like crystalline particles, which if compressed expresses aqueous phase provides the properties of sufficient firmness, thermal stability, and aqueous phase expression.

SUMMARY OF THE INVENTION

This invention embodies a rheological solid shave composition comprising crystallizing agents; optionally, in combination with a device or implement. The crystallizing agents form a crystal mesh that provides for the rheological solid composition which immobilizes the composition which comprises water as well as soluble and non-soluble actives, and that further releases at least some of the composition during compression, for example during use on the skin.

In accordance with one aspect, a rheological solid shave composition is provided that comprises crystallizing agent; suspension agent; active; and an aqueous phase.

In accordance with one aspect, a process for the manufacture of a rheological solid composition is provided, the process comprising the following steps:

- providing an aqueous solution of sodium chloride and sodium hydroxide,
- heating the aqueous solution of sodium chloride and sodium hydroxide,
- adding an emulsifier, preferably palmitic acid, in order to obtain an emulsifier main mix, preferably a sodium palmitate soap main mix,
- adding a suspension agent, preferably xanthan gum and glycerin, to the emulsifier main mix,
- adding an active premix to the emulsifier main mix to obtain a blend, the active premix preferably being a petrolatum-based premix of actives,
- cooling the blend in order to form a crystalline structure of the rheological solidcomposition,
- optionally adding a hygroscopic stabilizer to the blend in order to stabilize the crystalline structure, the hygroscopic stabilizer preferably being sodium lactate.

The crystallizing agent comprises a salt of fatty acids containing from about 13 to about 20 carbon atoms.

The rheological solid shave composition has a firmness between about 0.1 N to about 50.0 N as determined by the FIRMNESS TEST METHOD.

The rheological solid shave composition has a thermal stability of about 40° C. to about 95° C. as determined by the THERMAL STABILITY TEST METHOD.

The rheological solid shave composition has a liquid expression of between about 100 J m-3 to about 8,000 J m-3 as determined by the AQUEOUS PHASE EXPRESSION TEST METHOD.

The composition comprises water. The composition may further comprise soluble and/or non-soluble actives that may provide further benefits before, during or after shaving. The soluble and non-soluble actives may include traditional shave treatment actives such as humectants, moisturizers, oils, sensates, fragrances, lubricants and the like. In addition to traditional shave treatment actives, such optional actives include treatment for wrinkles, dark spots, moisturization, UV protection, anti-aging, superficial scarring, pre-cancerous skin spots, ex-folinates agents, chemical peels, pore moisturizers, anti-oxidants, retinol, acne treatment and treatment peptides.

The rheological solid shave composition may include a suspension agent

The rheological solid shave composition may be attached to a hair removal device such as a razor or may be separate from any such hair removal device. Where is it attached to a hair removal device the rheological solid shave composition may take the form of a lubri-strip, a wing, or any other on-board form. Where the rheological solid shave composition is separate from any hair removal device it may take the form of a stick, cylinder, button, gummy bear, sphere in a single container. Alternately, the rheological solid shave composition may be incorporated into an implement that is not a hair removal device such as an applicator or stick dispenser. The rheological solid shave composition may also be used separately from or in combination with, any hair removal device.

Also provided is a method of producing a shave rheological solid composition that comprises providing water; providing a crystallizing agent; providing NaCl; wherein the NaCl is about 10% or less per weight percentage of the rheological solid composition; mixing the water, crystallizing agent, and NaCl; heating the mixture; cooling the mixture; producing a rheological solid composition wherein the wherein, the rheological solid composition, has a firmness between about 0.1 N to about 50.0 N as determined by the FIRMNESS TEST METHOD; a thermal stability greater than about 54° C. as determined by the THERMAL STABILITY TEST METHOD; a liquid expression of between about 300 J m-3 to about 9,000 J m-3 as determined by the AQUEOUS PHASE EXPRESSION TEST METHOD.

Also provided is a method of producing a shave rheological solid composition that comprises providing water; providing a crystallizing agent; mixing the water and crystallizing agent; heating the mixture; cooling the mixture to produce a rheological solid composition; adding NaCl to the rheological solid composition; wherein, the rheological solid composition after addition of the NaCl, has a firmness between about 0.1 N to about 50.0 N as determined by the FIRMNESS TEST METHOD; a thermal stability greater than about 55° C. as determined by the THERMAL STABILITY TEST METHOD; a liquid expression of between about 300 J m-3 to about 9,000 J m-3 as determined by the AQUEOUS PHASE EXPRESSION TEST METHOD.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

The present invention includes a rheological solid shave composition comprising a crystalline mesh. The crystalline mesh ("mesh") comprises a relatively rigid, three-dimensional, interlocking crystalline skeleton frame of fiber-like crystalline particles (formed from crystallizing agents), having voids or openings containing aqueous solution and optionally one or more actives. The mesh provides a self-supporting structure, such that a rheological solid composition may 'stand on its own' when resting on a surface. If compressed above a critical stress, the mesh allows the rheological solid composition to express the entrapped aqueous phase, and optionally water soluble actives. The rheological solid compositions of the present invention include crystallizing agent(s), aqueous phase and optionally active and may be combined with a device to enable application.

It is surprising that it is possible to prepare rheological solid compositions that exhibit sufficient firmness, aqueous phase expression and thermal stability. Not wishing to be bound by theory, it is believed that sodium carboxylates present in high-water compositions (e.g. above about 80%) and correct chain length purity may form elongated, fiber-like crystal habits. These crystals form mesh structures that result in rheological solid compositions even at very low concentrations. Firmness may be achieved by carefully adjusting the concentration and chain length distribution of the crystallizing agent. Aqueous phase expression may be achieved from these rheological solid structures, by compression above a yield behavior that breaks the mesh structure allowing the water to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize when heated above 40° C. This is an important property in relation to the shelf-life and supply chain for consumer products. Addition of sodium chloride can be used to increase the thermal stability of the composition but should be added correctly to ensure the proper formation of the mesh. These discovered design elements stand in contrast to compositions prepared with too-soluble a gelling agent to be practically thermal stable. Finally, such rheological solid compositions are prepared by cooling the mixture largely quiescently, in contrast to freezer or other mechanically invasive processes. Not wishing to be bound by theory, quiescent processes allow the formation of very large and efficient fibrous crystals rather the breaking them into smaller less efficient crystals.

Crystallizing Agent(s)

Figure 1:
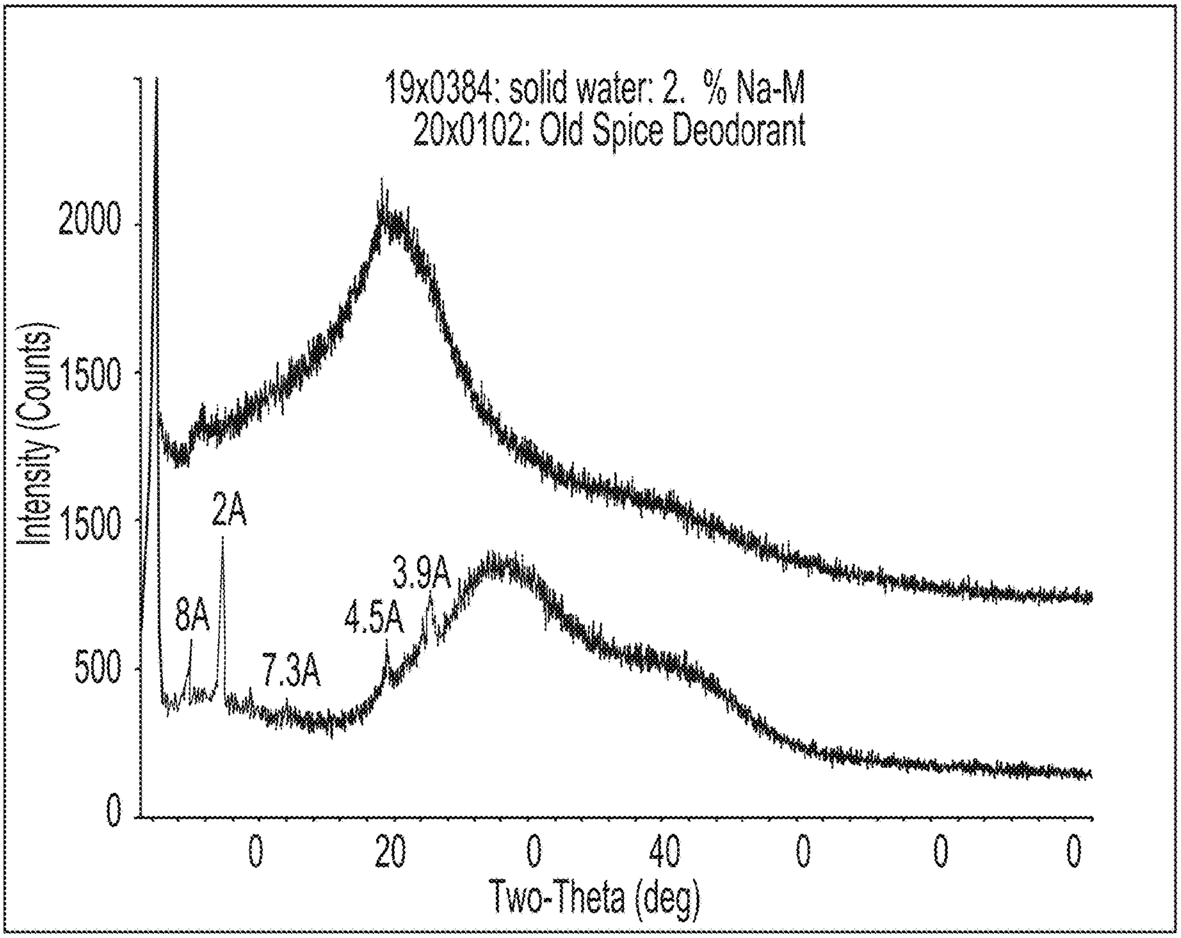
FIG. 1. is a X-ray Diffraction Pattern

In the present invention, the mesh of a rheological solid composition includes fiber-like crystalline particles formed from crystallizing agents. "Crystallizing agent" as used herein includes sodium salts of fatty acids with shorter chain length (C13-C20), such as sodium palmitate (C16). Commercial sources of crystallizing agent usually comprise complicated mixtures of molecules, often with chain lengths between C10 to C22. The rheological solid compositions are best achieved with a 'narrow blend'—or distribution of crystallizing agent chain lengths, further best achieved with blends in the absence of very short chain lengths (C12 or shorter) and/or measurable amounts of unsaturation on the chains of the fatty acid sodium salts, and best achieved with a single chain length between C13 to C20, coupled with a controlled crystallizing processing. Accordingly, rheological solid compositions are best achieved when the chain length distribution of the crystallizing agent is preferably greater than about Po>0.3, more preferably about Po>0.5, more preferably about Po>0.6, more preferably about Po>0.7 and most preferably about Po>0.8, as determined by the BLEND TEST METHOD. One skilled in the art, recognizes crystalline particles as exhibiting sharp scattering peaks between 0.25-60 deg. 2θ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
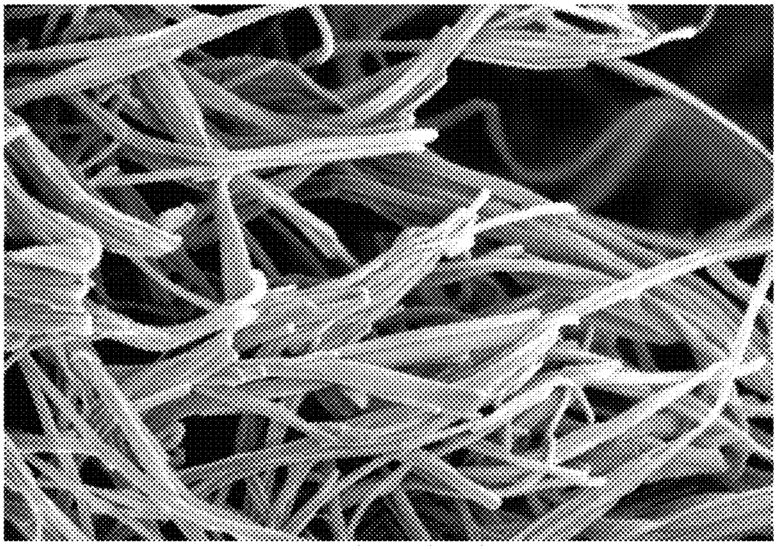
FIG. 2. is a SEM of Interlocking Mesh
Figure 3:
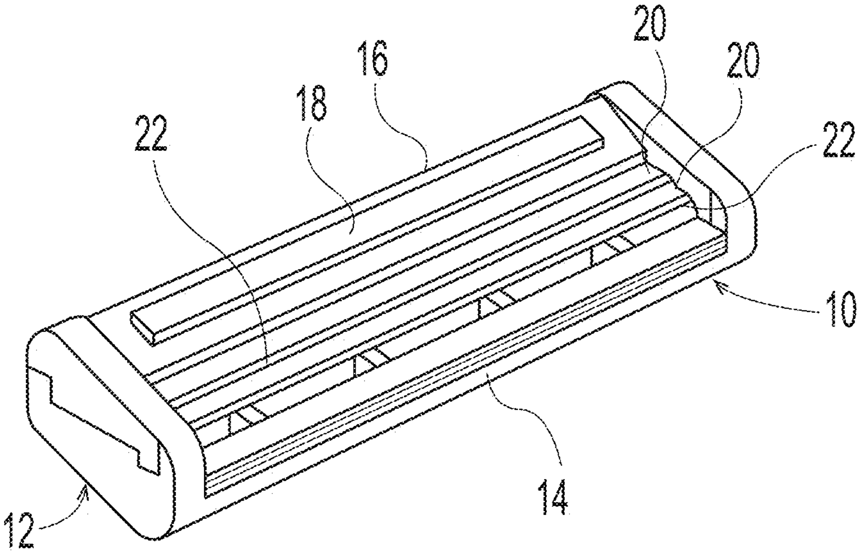
FIG. 3. is a perspective view of a razor cartridge comprising a rheological solid composition as a shaving aid in accordance with the present disclosure.
Figure 4A:
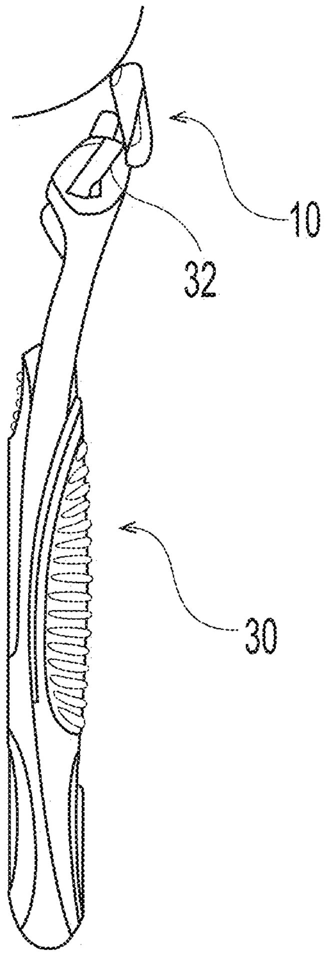
FIG. 4A. is a side view of a razor comprising a rheological solid composition as a shaving aid in the form of a lubri-strip in accordance with the present disclosure.
Figure 4B:
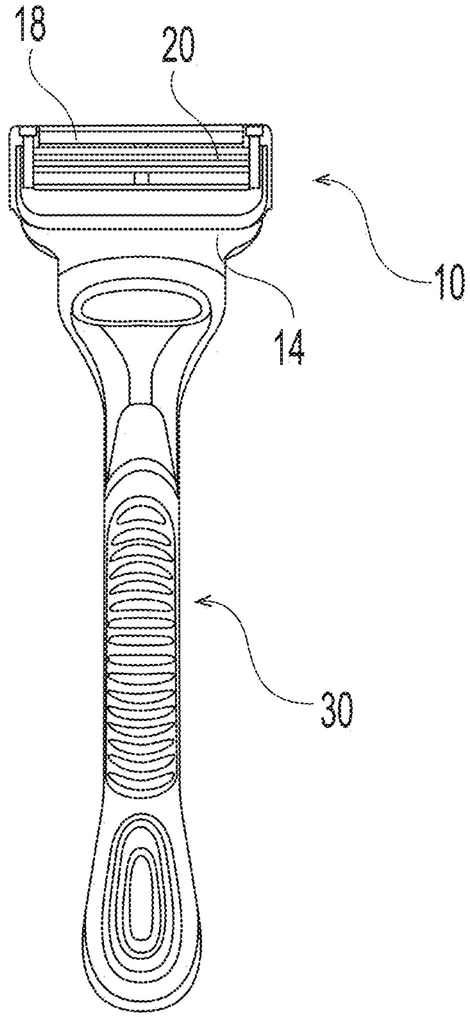
FIG. 4B. is a front view of a razor comprising a rheological solid composition as a shaving aid in the form of a lubri-strip in accordance with the present disclosure.
Figure 5A:
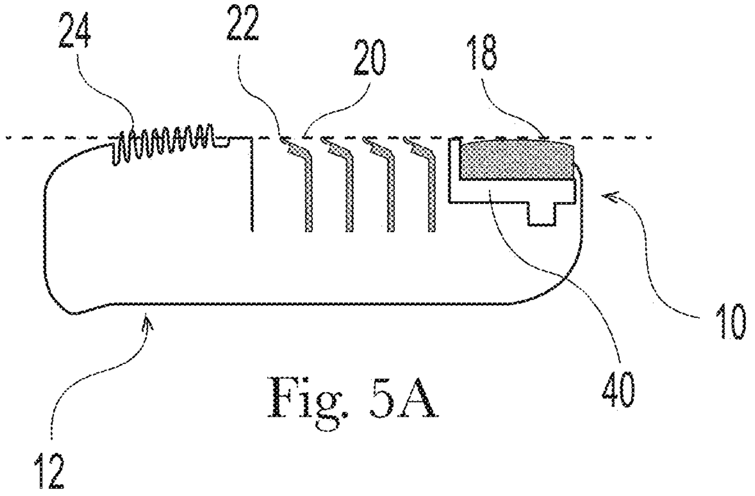
FIG. 5A. is a cut-through view of a razor cartridge comprising a rheological solid composition as a shaving aid in the form of a solid contained within a box or tray in accordance with the present disclosure.
Figure 5B:
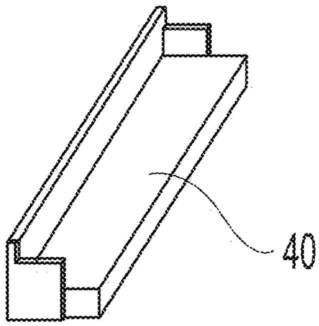
FIG. 5B. is a perspective view of a tray that may contain the solid shaving aid comprising the rheological solid composition.
Figure 5C:
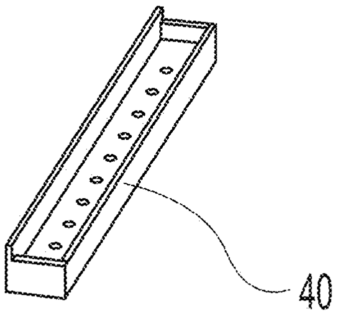
FIG. 5C. is a perspective view of a tray that may contain the solid shaving aid comprising the rheological solid composition.

Rheological solid compositions of the present invention comprise greater than about 80% water and are 'structured' by a mesh of interlocking, fiber-like crystalline particles of mostly single-chain length, as described above, see (FIG. 2). The term 'fiber-like crystalline particle' refers to a particle in which the length of the particle in the direction of its longest axis is greater than 10× the length of the particle in any orthogonal direction. The fiber-like crystalline particles produce a mesh at very low concentrations (~0.5 wt %) which creates a solid that yields with a minimum applied stress—i.e. rheological solid. The aqueous phase primarily resides in the open spaces of the mesh. In preparing these compositions, the crystallizing agent is dissolved in aqueous phase using heat. The fiber-like crystalline particles form into the mesh as the mixture cools over minutes to hours.

Chain Length Blends

Effective chain length blends allow the creation of effective mesh microstructures in rheological solid compositions. In fact, adhoc (or informed selection) of crystallizing agents often leads to liquid or very soft compositions. The crystallizing agent may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—or the quantitative weight fraction of each chain length in the crystallizing agent, can be determined by the BLEND TEST METHOD, as described below. Commercial sources of crystallizing agent usually comprise complicated mixtures of molecules, often with chain lengths between 10 to 22.

Rheological solid compositions of the present invention have preferred chain length blends, as described by 'Optimal Purity' (Po) and 'Single Purity' (Ps), determined by the BLEND TEST METHOD. Sodium carboxylate crystallizing agents can have an 'Optimal Chain Length' of between 13 to 22 carbons and can be used alone or combined to form mesh structures that satisfy all three performance criteria of a rheological solid composition. Not wishing to be bound by theory, it is believed that these chain length molecules (13 to 22) have a high solubilization temperature (e.g. Krafft Temperature) and can pack into crystals efficiently. Sodium carboxylate crystallizing agents can have 'Unsuitable Chain Length' crystallizing agents have chain length of sodium carboxylate molecules of 10, 12, 18:1 and 18:2 (and shorter or other unsaturated chain lengths). When present in compositions alone or in some combinations with 'optimal chain length' molecules, they do not form rheological solid composition that meet the required performance criteria. Accordingly, inventive compositions require the proper blend of crystallizing agent molecules, to ensure the proper properties of the rheological solid composition. Po describes the total weight fraction of optimal chain length molecules of crystallizing agent to the total weight of crystallizing agent molecules, that is preferably Po>0.4, more preferably Po>0.6, more preferably Po>0.8 and most preferably Po>0.90. Ps describes the total weight fraction of the most common chain length molecule in the crystallizing agent to the total weight of crystallizing agent, that is preferably Ps>0.5, more preferably Ps>0.6, more preferably Ps>0.7, more preferably Ps>0.9.

Aqueous Phase

The rheological solid shave composition includes an aqueous carrier. The aqueous carrier which is used may be distilled, deionized, or tap water. Water may be present in any amount for the rheological solid composition to be an aqueous solution. Water may be present in an amount of about 80 wt % to 99.5 wt %, alternatively about 90 wt % to about 99.5 wt %, alternatively about 92 wt % to about 99.5 wt %, alternatively about 95 wt %, by weight of the rheological solid composition. The aqueous phase may contain a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. The level of monohydric alcohol may about 1 wt % to about 5 wt %, alternatively less than about 6 wt %, alternatively less than about 3 wt %, alternatively less than about 1 wt %, by weight of the rheological solid composition. Low molecular weight monohydric alcohols may be present in the rheological solid composition due to the addition of these alcohols to such ingredients as perfumes and as stabilizers for some preservatives or due to impurities.

The aqueous phase may contain shave actives. The shave actives may be soluble in the aqueous carrier or may be dispersed therein.

Solvents

The composition can contain a solvent. Non-limiting examples of solvents can include ethanol, glycerol, propylene glycol, polyethylene glycol 400, polyethylene glycol 200, and mixtures thereof. In one example the composition comprises from about 0.5% to about 15% solvent, in another example from about 1.0% to about 10% solvent, and in another example from about 1.0% to about 8.0% solvent, and in another example from about 1% solvent to about 5% solvent.

The aqueous phase may contain perfumes to the extent that the perfume is soluble in the aqueous phase or can be made soluble through the use of solvents. The shave composition may include non water soluble perfumes. Non water soluble perfumes may be incorporated as insoluble actives.

Lubricant

The shave composition may comprise a lubricant. The lubricant may comprise a water soluble polymer. The lubricant may be at least partially soluble in the aqueous phase. The lubricant may be at least partially non-dissolved in the aqueous phase and dispersed therein.

The lubricant provides lubrication during the shave. Examples of suitable water soluble polymers may include polyethylene oxide (PEO), polyvinyl pyrrolidone, polyacrylamide, polyhydroxymethacrylate, polyvinyl imidazoline, polyethylene glycol (PEG), polyvinyl alcohol, polyhydroxyethymethacrylate, copolymers of PEO and polypropylene oxide (PPO), guars, celluloses, modified celluloses, and mixtures thereof. Preferably, the water soluble polymer is PEO, and in some examples, the water soluble polymer may be selected from high and/or low molecular weight PEO referred to in the industry as PEO and PEG respectively.

According to the present disclosure, the shaving aid may comprise a lubricant comprising from about 1% to about 99% by weight of the shaving aid, preferably at least about 15%, more preferably at least about 20%, most preferably at least about 25%, and up to about 70%, preferably up to about 60% by weight of the shaving aid. The lubricating material preferably comprises at least 50% PEO by weight of the lubricant.

The water soluble polymer (especially PEO) may have a number-average molecular weight of at least about 20,000 g/mol, preferably at least about 50,000, more preferably at least about 100,000 or from about 100,000 to about 10 million, or about 300,000 to about 8 million, or from about 1 million to about 5 million or about 2 million to about 3 million. The PEO may have a number-average molecular weight of about 5 million (all values are ±10,000 g/mol).

The PEO may include a blend of different PEOs of differing molecular weights so that the weighted-average of the component PEO's fall within the desired molecular weight range for the PEO. The PEO blend may comprise about 40% to 80% of PEO having an average molecular weight of about 5 million (e.g. POLYOX™ Coagulant; Dow Chemical) and about 60% to 10% of PEO having an average molecular weight of about 300,000 (e.g. POLYOX™ WSR-N-750; Dow Chemical). The PEO blend may comprise about 40% to 80% of PEO having an average molecular weight of about 8 million (e.g. POLYOX™ 308) and about 60% to 10% of PEO having an average molecular weight of about 300,000 (e.g. POLYOX™ WSR-N-750; Dow Chemical). The PEO blend may also advantageously contain up to about 10% (for example about 5%) by weight of a low molecular weight (i.e. MW<10,000) PEG such as PEG-100.

Suitable copolymers of PEO and PPO may have an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the shaving aid in aqueous conditions, especially in combination with a further water soluble polymer (particularly PEO), and thus prevent an undesirable feeling in use.

The PEO/PPO copolymer may advantageously be a block copolymer, preferably a tri-block copolymer having the sequence: PEO—PPO-PEO, the latter being commercially available under tradenames such as PLURACARE® (BASF) and PLURONIC® (BASF).

The PEO/PPO copolymer may have a weight ratio of PEO to PPO, of from 1000:1 to 1:1000 or from 100:1 to 1:100. The PEO/PPO copolymer is typically present at an amount of from 0.01% to 50%, preferably from 0.01% to 50%, more preferably from 2% to 40%, even more preferably from 3% to 25%, even more preferably still from 4% to 20% and most preferably from 5% to 10% by weight of the lubricating material or by weight of the shaving aid.

The shaving aid and/or water soluble polymer preferably comprises less than 5%, preferably less than 1% by weight and more preferably is/are substantially free of lathering soaps (i.e. salts of fatty $C_4$ to $C_{30}$ acids) and lathering surfactants. A lathering surfactant is defined as a surfactant which when combined with water and mechanically agitated, generates a foam or lather. Lathering surfactants may include anionic and amphoteric lathering surfactants and mixtures thereof. Anionic lathering surfactants may include sarcosinates, sulfates, sulfonate, isethionate, taurates, phosphates, lactylates, glutamates, alkali metal salts of fatty acids (i.e. soaps) having from 8 to 24 carbons, and mixtures thereof.

The shave composition may comprise an anti-oxidant. The anti-oxidant may be included with the aqueous phase or separately from the aqueous phase. The anti-oxidant may, among other things, help ensure the stability of the lubricant particularly where the composition experiences elevated temperatures, for example during processing or during shipping. The anti-oxidant may include multi-component anti-oxidant systems such as systems that comprise chelants. The chelants may help mitigate the impact of ionic impurities in the composition.

Anti-oxidants useful in the present invention are disclosed in U.S. application Ser. No. 17/089,867, entitled "Shaving Aid Comprising an Antioxident" filed on Nov. 5, 2020 which is incorporated by reference herein.

Sensate

The shave composition may comprise a sensate. The sensate may be at least partially soluble in the aqueous phase. The sensate may be at least partially non-dissolved in the aqueous phase and dispersed therein. The sensate may be insoluble in the aqueous phase.

Sensate

In embodiments, soluble or insoluble active agent can include one or more components that provide a sensory benefit, often called a sensate. Sensates can have sensory attributes such as a warming, tingling, or cooling sensation. Suitable sensates include, for example, menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal known as CGA, Winsense WS-5 supplied by Renessenz-Symrise, Vanillyl butyl ether known as VBE, and mixtures thereof.

In certain embodiments, the sensate comprises a coolant. The coolant can be any of a wide variety of materials. Included among such materials are carboxamides, menthol, ketals, diols, and mixtures thereof. Some examples of carboxamide coolants include, for example, paramenthan carboxyamide agents such as N-ethyl-p-menthan-3-carboxamide, known commercially as "WS-3", N,2,3-trimethyl-2-isopropylbutanamide, known as "WS-23," and N-(4-cyanomethylphenyl)-p-menthanecarboxamide, known as G-180 and supplied by Givaudan. G-180 generally comes as a 7.5% solution in a flavor oil, such as spearmint oil or peppermint oil. Examples of menthol coolants include, for example, menthol; 3-1-menthoxypropane-1,2-diol known as TK-10, manufactured by Takasago; menthone glycerol acetal known as MGA manufactured by Haarmann and Reimer; and menthyl lactate known as Frescolat® manufactured by Haarmann and Reimer. The terms menthol and menthyl as used herein include dextro- and levorotatory isomers of these compounds and racemic mixtures thereof.

In certain embodiments, the sensate comprises a coolant selected from the group consisting of menthol; 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-p-menthanecarboxamide, and combinations thereof. In further embodiments, the sensate comprises menthol; N,2,3-trimethyl-2-isopropylbutanamide.

In some aspects, the sensate comprises a warming sensates. Non-limiting examples of warming sensates can include vanillyl alcohol n-butyl ether (sold as TK-1000 by Takasago International), vanillyl butyl ether (commercially available as HotFlux® from Corum, Inc., Taipei, Taiwan), capsaicin, nonivamide, ginger, capsicum (commercially available as Vegetol® Capsicum LC481 from Gattefossé, Lyon, France), and combinations thereof.

In some aspects, the sensate comprises a tingling sensate. Non-limiting examples of tingling sensates can include sichuan pepper, hydroxy alpha sanshool, jambu extracts, spilanthol, and combinations thereof. A suitable sensory enhancer can include a neuro-soother such as Mariliance™ available from Givaudan, Vernier, Switzerland.

One advantage to including a sensate is that they can provide a topical sensory effect. When the rheological solid shave composition having one or more sensates is applied to the skin, it can provide an on-skin sensation that can work in unison with the smell to provide an increased perception of product strength.

The rheological solid shave composition can comprise from about 0.001 to about 1.5 wt. % of a sensate, alternatively from about 0.01 to about 1 wt. %, alternatively from about 0.1 to about 0.75 wt. %, alternatively from about 0.2 wt. % to about 0.5 wt. %, all by weight of the rheological solid shave composition.

Suspension Agent(s)

The suspension agent prevents the separation of insoluble actives in the preparation of the rheological solid shave composition. Inventive compositions are heated until the crystallizing agent is dissolved leaving a dispersed active in a low viscosity fluid. When the compositions are cooled, the crystallizing agent begins to form fiber-like crystalline particles which weave together into the mesh, which eventually traps the actives. This process can take minutes to hours. Not wishing to be bound by theory, it is believed that the suspension agents increase viscosity or create a yield stress that holds the actives from creaming or sedimenting during the crystallization of the crystallizing agent and formation of the mesh. Preferred suspension agents are effective at low concentrations to prevent potential negative effects on the mesh and performance of the consumer product. Preferred levels are below about 2 wt. %, alternatively below about 1 wt. %, alternatively below about 0.5 wt. %, alternatively below about 0.1 wt. %. In some aspects, the rheological solid shave composition can comprise from about 0.01 to about 2 wt. % of a suspension agent, alternatively from about 0.05 to about 1 wt. %, alternatively from about 0.1 to about 0.5 wt. %, all by weight of the rheological solid shave composition.

Suitable suspension agents include gums, polymers, microfiber particles, clay particles, and combinations thereof, and unexpectedly must be selected for a composition such that their addition does not have a negative effect on the mesh. For example, the use of gums can weaken the mesh structure relative to compositions that do not contain gums, requiring an increase in the amount of crystallize agent (Example 2). As another example, use of clays (Example 10) and microfibers (Example 9) can be rendered ineffective with the addition of sodium chloride.

Gums

The rheological solid shave composition includes at least one suspension agent to keep insoluble materials (i.e. solids or oils) suspended during preparation. The suspension agent may include one or more biopolymers. Non-limiting examples of such biopolymers include polysaccharides such as polymers of glucose, fructose, galactose, mannose, rhamnose, glucuronic acid, and mixtures thereof.

The suspension agent may be in the form of a polysaccharide or mixture of polysaccharides. Preferable polysaccharide suspension agents include xanthan gum, glucomannan, galactomannan, and combinations thereof. The glucomannan may be derived from a natural gum such as konjac gum. The galactomannan may be derived from naturals gums such as locust bean gum. Polysaccharide suspension agents may also include carrageenan. Suspension agent gums may be modified such as by deacetylation.

The rheological solid shave composition may comprise a polysaccharide suspension agent system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of konjac gum, locust bean gum, tara bean, and combinations thereof.

Preferably, the first polysaccharide is xanthan gum and the second polysaccharide is konjac gum.

The first polysaccharide may be present at a level of greater than about 10 wt. % and less than about 100 wt. %, alternatively about 40 wt. % to about 90 wt. %, alternatively about 40 wt. % to about 60 wt. %, by weight of the polysaccharide suspension agent system.

The second polysaccharide may be present at a level of about 0 wt. % to about 90 wt. %, alternatively about 60 wt. % to about 10 wt. %, alternatively about 60 wt. % to about 40 wt. %, by weight of the polysaccharide suspension agent system.

The total concentration of polysaccharide present in the rheological solid shave composition may be between about 0.01-about 1.0 wt. %, or more preferably between about 0.03-about 1.0 wt. %, or more preferably between about 0.05-about 0.8 wt. %, more preferably between about 0.07-about 0.75 wt. %, and most preferably between about 0.09-about 0.5 wt. %, all by weight of the rheological solid shave composition. Without wishing to be bound by theory, it is believed that minimizing the total polysaccharide level in the composition ensures stability of the dispersed active agents during preparation while minimizing the effect of the suspension agent on the mesh structure.

The polysaccharide suspension agent system may have a weight-average molecular weight in the range of about 10,000 Daltons to about 15,000,000 Daltons, alternatively about 200,000 Daltons to about 10,000,000 Daltons, alternatively about 300,000 Daltons to about 6,000,000 Daltons, alternatively about 300,000 Daltons to about 500,000 Daltons.

The polysaccharide suspension agent system may be characterized by the average ratio of acetylation, wherein the average ratio of acetylation is the number of acetylated hydroxyl groups in the polysaccharide divided by the number of free hydroxyl groups in the polysaccharide. The average ratio of acetylation may be in the range of about 2.0 to about 0.5, preferably in the range of about 1.5 to about 0.5.

Clays

In the present disclosure, a suspension agent may be used to provide viscosity and thixotropic properties to the composition so that the suspended active agent particles are prevented from creaming or settling during preparation. In one or more embodiments, the suspension agent may be a mineral clay mixture and more particularly an organophilic mineral clay mixture. In one or more embodiments, the mineral clay mixture may be treated with alkyl quaternary ammonium compounds in order to render the mineral clay mixture hydrophobic; such clays may also be termed organophilic. In one or more embodiments, the mineral clay mixtures can comprise: a mineral clay (a) comprising from about 50 to about 95 wt. %, based on the weight of the mineral clay mixture, or from about 60 to about 95 wt. %, or from about 70 to about 90 wt. %, of a mineral clay selected from the group consisting of sepiolite, palygorskite, and mixtures of sepiolite and palygorskite; and a mineral clay (b) comprising the balance, by weight of the mineral clay mixture, of a smectite. In one or more embodiments, the smectite may be a natural or synthetic clay mineral selected from the group consisting of hectorite, laponite, montmorillonite, bentonite, beidelite, saponite, stevensite, and mixtures thereof. Suitable clays include Laponite from the Garamite line of products available from BYK Additives, (Gonzalez, TX).

Microfibers

Any microcrystalline cellulose may be employed in the compositions of the present invention. Suitable feedstocks include, for example, wood pulp such as bleached sulfite and sulfate pulps, corn husks, bagasse, straw, cotton, cotton linters, flax, kemp, ramie, fermented cellulose, etc. The amounts of microcrystalline cellulose and hydrocolloid may be varied over a wide range depending upon the properties desired in the final composition. Suitable microfibers include Rheocrysta c-2sp (WASE COSFA USA, Inc.).

Insoluble Active(s)

The rheological solid shave composition may include one or more insoluble active particles besides the fiber-like crystalline particles that comprise the mesh. As used herein, an "insoluble active particle" comprises at least a portion of a solid, a semi-solid, or liquid material, including some amount of insoluble active. The insoluble active particles may take various different forms, for example the insoluble active particles may be 100 wt. % solid or may be hollow. The insoluble active particles may include, for example, mesoporous particles, activated carbon, zeolites, benefit agent delivery particles, waxes, insoluble oils, hydrogels, and/or ground nutshells.

In some aspects, the rheological solid shave composition can comprise from about 0.001 to about 25 wt. % insoluble active particles, alternatively from about 0.1 to about 15 wt. %, alternatively from about 0.5 to about 12 wt. %, alternatively from about 1 to about 10 wt. %, alternatively from about 5 to about 10 wt. %, all by weight of the rheological solid shave composition.

In some aspects, the rheological solid shave composition can comprise from about 0.001 to about 25 wt. % insoluble active, alternatively from about 0.1 to about 15 wt. %, alternatively from about 0.5 to about 12 wt. %, alternatively from about 1 to about 10 wt. %, alternatively from about 5 to about 10 wt. %, all by weight of the rheological solid shave composition.

The rheological solid shave composition may include one or more types of insoluble active particles, for example, two insoluble active particles types, wherein one of the first or second insoluble active particles (a) is made of a different material than the other; (b) has a wall that includes a different amount of wall material or monomer than the other; (c) contains a different amount of perfume oil ingredient than the other; (d) contains a different perfume oil; (e) has a wall that is cured at a different temperature; (f) contains a perfume oil having a different c Log P value; (g) contains a perfume oil having a different volatility; (h) contains a perfume oil having a different boiling point; (i) has a wall made with a different weight ratio of wall materials; (j) has a wall that is cured for different cure time; and/or (k) has a wall that is heated at a different rate.

The plurality of insoluble active agent particles may have a diameter of less than about 500 μm, alternatively less than about 400 μm, alternatively less than about 300 μm, alternatively less than about 200 μm, alternatively less than about 100 μm. One skilled in the art recognizes that the ability to suspend particles is a function of the mean diameter of the particles (where larger particles are more difficult to suspend) and a function of the total amount of the particles (where large amounts of particles are more difficult to suspend).

To the former, one skilled in the art further recognizes that the concentration of the suspension agent with a given insoluble active agent may have to be increased to accommodate larger insoluble active particles. It is generally preferred to minimize the amount of suspension agent (e.g. Example 2) so that smaller active agent particles are preferred. To the latter, one skilled in the art further recognizes that the concentration of the suspension agent with a given insoluble active agent may have to be increased to accommodate larger amounts of insoluble active particles (e.g. Example 7).

Encapsulated Insoluble Benefit Agent

The insoluble active particle may include a wall material that encapsulates an insoluble active. The insoluble active may be selected from the group consisting of: perfume compositions, perfume raw materials, perfume, skin coolants, vitamins, sunscreens, antioxidants, glycerin, bleach encapsulates, chelating agents, antistatic agents, insect and moth repelling agents, colorants, antioxidants, sanitization agents, disinfecting agents, germ control agents, mold control agents, mildew control agents, antiviral agents, drying agents, stain resistance agents, soil release agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin agents, natural actives, antibacterial actives, antiperspirant actives, cationic polymers, dyes, metal catalysts, non-metal catalysts, activators, pre-formed peroxy-carboxylic acids, diacyl peroxides, hydrogen peroxide sources, enzymes, topical drug actives, and combinations thereof. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

The wall material of the insoluble active particle may comprise melamine, polyacrylamide, silicones, silica, polystyrene, polyurea, polyurethanes, polyacrylate based materials, polyacrylate ester-based materials, gelatine, styrene malic anhydride, polyamides, aromatic alcohols, polyvinyl alcohol and mixtures thereof. The polyacrylate based wall materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

The polyacrylate ester-based wall materials may comprise polyacrylate esters formed by alkyl and/or glycidyl esters of acrylic acid and/or methacrylic acid, acrylic acid esters and/or methacrylic acid esters which carry hydroxyl and/or carboxy groups, and allylgluconamide, and mixtures thereof.

The aromatic alcohol-based wall material may comprise aryloxyalkanols, arylalkanols and oligoalkanolarylethers. It may also comprise aromatic compounds with at least one free hydroxyl-group, especially preferred at least two free hydroxy groups that are directly aromatically coupled, wherein it is especially preferred if at least two free hydroxy-groups are coupled directly to an aromatic ring, and more especially preferred, positioned relative to each other in meta position. It is preferred that the aromatic alcohols are selected from phenols, cresols (o-, m-, and p-cresol), naphthols (alpha and beta-naphthol) and thymol, as well as ethylphenols, propylphenols, fluorphenols and methoxyphenols.

The polyvinyl alcohol based wall material may comprise a crosslinked, hydrophobically modified polyvinyl alcohol, which comprises a crosslinking agent comprising i) a first dextran aldehyde having a molecular weight of from about 2,000 to about 50,000 Da; and ii) a second dextran aldehyde having a molecular weight of from greater than about 50,000 to about 2,000,000 Da.

Preferably, the insoluble active particle with perfume has a wall material comprising silica or a polymer of acrylic acid or derivatives thereof and a benefit agent comprising a perfume mixture.

With regards to insoluble active particles, the rheological solid shave composition may contain from about 0.001 wt. % to about 20 wt. %, by weight of the rheological solid shave composition, of a benefit agent contained with the wall material of the benefit agent delivery particle. Or, the rheological solid shave composition may contain from about 0.01 wt. % to about 10 wt. %, or most preferably from about 0.05 wt. % to about 5 wt. %, by weight of the rheological solid shave composition, of a benefit agent contained with the wall material of the insoluble active particle.

These walled particles may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof.

Unencapsulated Perfume

The rheological solid shave composition may include unencapsulated perfume comprising one or more perfume raw materials that solely provide a hedonic benefit (i.e. that do not neutralize malodors yet provide a pleasant fragrance). Suitable perfumes are disclosed in U.S. Pat. No. 6,248,135. For example, the rheological solid shave composition may include a mixture of volatile aldehydes for neutralizing a malodor and hedonic perfume aldehydes.

Where perfumes, other than the volatile aldehydes in the malodor control component, are formulated into the rheological solid shave composition, the total amount of perfumes and volatile aldehydes may be from about 0.015 wt. % to about 2 wt. %, alternatively from about 0.01 wt. % to about 1.0 wt. %, alternatively from about 0.015 wt. % to about 0.5 wt. %, by weight of the rheological solid shave composition.

Perfume Delivery Technologies

The rheological solid shave compositions may comprise one or more perfume delivery technologies that stabilize and enhance the deposition and release of perfume ingredients from a treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

The rheological solid shave compositions may comprise from about 0.001 wt. % to about 20 wt. %, or from about 0.01 wt. % to about 10 wt. %, or from about 0.05 wt. % to about 5 wt. %, or even from about 0.1 wt. % to about 0.5 wt. %, by weight of the perfume delivery technology. In one aspect, the perfume delivery technologies may be selected from the group consisting of: pro-perfumes, polymer particles, soluble silicone, polymer assisted delivery, molecule assisted delivery, assisted delivery, amine assisted delivery, cyclodextrins, starch encapsulated accord, zeolite and inorganic carrier, and mixtures thereof.

The perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically, the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Essential and Natural Oils

The insoluble active particle may include individual mixtures of insoluble oils such as essential and natural oils. The term "essential oils" as used herein refers to oils or extracts distilled or expressed from plants and constituents of these oils. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, β-pinene, limonene), orange (limonene, citral), anise (anethole, safrol), clove (eugenol, eugenyl acetate, caryophyllene), rose (geraniol, citronellol), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene), wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), eucalyptus oil, nutmeg oil, turpentine oil, chamomile oil, neroli oil, cedar leaf (α-thujone, β-thujone, fenchone), and combinations thereof. Essential oils are widely used in perfumery and as flavorings, medicine, and solvents. Essential oils, their composition and production, are described in detail in Kirk-Othmer Encyclopedia of Chemical Technology, $4^{th}$ Edition and in The Merck Index, $13^{th}$ Edition.

In some aspects, the rheological solid shave composition can comprise from about 0.1 to about 20 wt. % insoluble oils, alternatively from about 0.5 to about 15 wt. %, alternatively from about 1 to about 12 wt. %, alternatively from about 4 to about 10 wt. %, all by weight of the rheological solid shave composition.

Waxes and Oils

The insoluble active particle may include individual mixtures of waxes and oils as a non-aqueous vehicle. The non-aqueous vehicle is generally any chemical in any physical form that does not contain water. The non-aqueous vehicle can be selected from the group consisting of liquid petrolatum, petrolatum, mineral oil, glycerin, natural and synthetic oils, fats, silicone and silicone derivatives, polyvinylacetate, natural and synthetic waxes such as animal waxes like beeswax, lanolin and shellac, hydrocarbons, hydrocarbon derivatives, vegetable oil waxes such as carnauba, candelilla and bayberry wax, vegetable oils such as caprylic/capric triglycerides, and combinations thereof. In some aspects, the non-aqueous vehicle can be selected from the group consisting of liquid petrolatum, petrolatum, mineral oil, vegetable oils such as apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, and animal oil such as fish oil and oleic acid, and mixtures thereof. In some aspects, the non-aqueous vehicle can be mineral oil. In some aspects, the non-aqueous vehicle can be pentaerythrityl tetraisostearate.

Preferably, the non-aqueous vehicle is hydrophobic. One advantage to adding a hydrophobic non-aqueous vehicle, such as petrolatum, is temperature stability. Not wishing to be bound by theory, it is believed that the addition of a hydrophobic non-aqueous vehicle can provide better partitioning between the oil phase and aqueous phase, which can provide temperature stability. In addition, a hydrophobic non-aqueous vehicle can improve the hardness and spreadability of the rheological solid shave composition.

In some aspects, the rheological solid shave composition can comprise from about 1 to about 15 wt. % non-aqueous vehicle, alternatively from about 3 to about 12 wt. %, alternatively from about 5 to about 10 wt. %, all by weight of the rheological solid shave composition.

Suitable oils for use herein include for example natural oils, synthetic oils, silicone oils, petrolatum, triglycerides, butters or mixtures thereof. As used herein, the term "oil" includes, but is not limited to any non-aqueous substance that is very slightly soluble or practically insoluble in water according to the USP definition.

The oil may be selected from natural oil, synthetic oil, silicone oil and mixtures thereof. Non-limiting examples of suitable natural oils include Acetylated Castor Oil, Acetylated Hydrogenated Castor Oil, *Actinidia chinensis* (Kiwi), Seed Oil, *Adansonia digitata* Oil, *Aleurites moluccana* Seed Oil, *Anacardium occidentale* (Cashew) Seed Oil, *Arachis hypogaea* (Peanut) Oil, *Arctium lappa* Seed Oil, *Argania spinosa* Kernel Oil, *Argemone mexicana* Oil, *Avena sativa* (Oat) Kernel Oil, *Bertholletia excelsa* Seed Oil, *Borago officinalis* Seed Oil, *Brassica campestris* (Rapeseed) Seed Oil, *Calophyllum tacamahaca* Seed Oil, *Camellia japonica* Seed Oil, *Camellia kissi* Seed Oil, *Camellia oleifera* Seed Oil, Canola Oil, Caprylic/Capric/Lauric Triglyceride, Caprylic/Capric/Linoleic Triglyceride, Caprylic/Capric/Mystic/Stearic Triglyceride, Caprylic/Capric/Stearic Triglyceride, Caprylic/Capric Triglyceride, *Carthamus tinctorius* (Hybrid Safflower) Seed Oil, *Carthamus tinctorius* (Safflower) Seed Oil, *Carum carvi* (Caraway) Seed Oil, *Carya illinoensis* (Pecan) Seed Oil, Castor Oil Benzoate, *Chenopodium Quinoa* Seed Oil, Cibotium Barometz Oil, *Citrullus* Vulgaris (Watermelon) Seed Oil, *Cocos nucifera* (Coconut) Oil, Cod Liver Oil, *Coffea arabica* (Coffee) Seed Oil, *Coix lacryma-jobi* (Job's Tears) Seed Oil, *Corylus americana* (Hazel) Seed Oil, *Corylus avellana* (Hazel) Seed Oil, *Cucumis sativus* (Cucumber) Oil, *Cucurbita pepo* (Pumpkin) Seed Oil, *Daucus carota sativa* (Carrot) Seed Oil, *Elaeis guineensis* (Palm) Kernel Oil, *Elaeis guineensis* (Palm) Oil, *Gossypium* (Cotton) Seed Oil, *Helianthus annuus* (Hybrid Sunflower) Oil, *Helianthus annuus* (Sunflower) Seed Oil, *Hippophae rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis tinctoria* Seed Oil, *Juglans regia* (Walnut) Seed Oil, Lauric/Palmitic/Oleic Triglyceride, Umnanthes Alba (Meadowfoam) Seed Oil, *Unum usitatissimum* (Linseed) Seed Oil, *Lupinus albus* Seed Oil, *Macadamia integrifolia* Seed Oil, *Macadamia ternifolia* Seed Oil, Maleated Soybean Oil, *Mangifera indica* (Mango) Seed Oil, Marmot Oil, *Melaleuca alternifolia* (Tea Tree) Leaf Oil, *Melia azadirachta* Seed Oil, *Melissa officinalis* (Balm Mint) Seed Oil, Menhaden Oil, Mink Oil, *Moringa pterygosperma* Seed Oil, *Mortierella* Oil, Neatsfoot Oil, *Nelumbium speciosum* Flower Oil, *Nigella sativa* Seed Oil, *Oenothera biennis* (Evening Primrose) Oil, *Olea europaea* (Olive) Fruit Oil, *Olea europaea* (Olive) Husk Oil, Orange Roughy Oil, *Orbignya cohune* Seed Oil, *Orbignya oleifera* Seed Oil, *Oryza sativa* (Rice) Bran Oil, *Oryza sativa* (Rice) Germ Oil, Ostrich Oil, Oxidized Corn Oil, Oxidized Hazel Seed Oil, *Papaver orientale* (Poppy) Seed Oil, *Passiflora edulis* Seed Oil, *Persea gratissima* (Avocado) Oil, *Pistacia vera* Seed Oil, Placental Lipids, *Prunus amygdalus amara* (Bitter Almond) Kernel Oil, *Prunus amygdalus dulcis* (Sweet Almond) Oil, *Prunus armeniaca* (Apricot) Kernel Oil, *Prunus avium* (Sweet Cherry) Seed Oil, *Prunus cerasus* (Bitter Cherry) Seed Oil, *Prunus persica* (Peach) Kernel Oil, *Pyrus malus* (Apple) Oil, *Ribes nigrum* (Black Currant) Seed Oil, *Ricinus communis* (Castor) Seed Oil, *Rosa canina* Fruit Oil, *Rosa moschata* Seed Oil, Salmon Oil, *Salvia hispanica* Seed Oil, *Santalum album* (Sandalwood) Seed Oil, *Sesamum indicum* (Sesame) Seed Oil, Shark Liver Oil, *Solanum lycopersicum* (Tomato) Seed Oil, Soybean Lipid, Sphingolipids, *Taraktogenos kurzii* Seed Oil, *Telphairia pedata* Oil, Vegetable Oil, *Vitis vinifera* (Grape) Seed Oil, *Zea mays* (Corn) Germ Oil, *Zea mays* (Corn) Oil mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane, silicone polyether block copolymers and mixtures thereof.

The emollient may contain a silicone polyether. Suitable silicone polyether copolymers may comprise from about 1% to 50%, by weight of PEO, from about 20% to about 90% by weight of PPO, and from about 1% to about 20% by weight of silicone. Preferably, the silicone polyether copolymer comprises at least about 40%, more preferably at least about 50%, most preferably at least about 60%, by weight of PPO. In addition, the silicone polyether copolymer preferably comprises at least about 10%, more preferably from at least about 15%, most preferably from about 15% to 30% by weight of PEO. Furthermore, the silicone polyether block copolymer comprises from 1% to 20%, preferably 10% to 20%, more preferably about 15% by weight of silicone.

Non-limiting examples of commercially available silicone oils include Dow Corning 200 fluid, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methylphenyl fluid (sold by General Electric Company) and 556 Cosmetic Grade Fluid (sold by Dow Corning Corp.), Silshine 151 (sold by Momentive), PH1555 and PH1560 (sold by Dow Corning) and Silwets such as Silwets 7210, 7230 and 7220 (available from by Momentive).

Suitable triglycerides, may have the following formula:

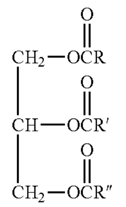

in which R, R', and R" may be the same as, or different from, one or both of the others, and in which each of R, R', and R" is a fatty acid and the triglyceride is solid at 25° C.

Suitable oils from which triglycerides may be formed include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, *Theobroma cacao* (Cocoa) Seed Butter, Cocoa Butter, *Mangifera indica* (Mango) Seed Butter, Kokum Butter and mixtures thereof. Particularly preferred are shea butter, cocoa butter and mixtures thereof.

Malodor Counteractants

The rheological solid shave composition may include other malodor reducing technologies. This may include, without limitation, amine functional polymers, metal ions, cyclodextrins, cyclodextrin derivatives, polyols, oxidizing agents, activated carbon, zeolites, and combinations thereof.

Feel Modifiers

The rheological solid shave composition may also include insoluble active agents designed to alter the feel properties of the composition when applied to surfaces, such as skin. This may include starches (e.g. tapioca starch, rice starch, or the like), talc, fumed silica (Aerosil® 200), titanium dioxide, dimethicone, iron oxide, mica, charcoal, colloidal oatmeal, colloidal cellulose, kaolin, and combinations thereof.

Skin Agents

Skin agents may be added to deliver a therapeutic and/or skin protective benefit. It will be recognized that of the numerous materials useful in the compositions delivered to skin, those that have been deemed safe and effective skin agent and mixtures thereof are logical materials for use herein. Such materials include Category I actives as defined by the U.S. Food and Drug Administration's (FDA) Tentative Final Monograph on Skin Protectant Drug Products for Over-the-Counter Human Use (21 C.F.R. § 347), which presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category DI actives as defined by the U.S. Food and Drug Administration's Tentative Final Monograph on Skin Protectant Drug Products for Over-the-Counter Human Use (21 C.F.R. § 347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, buffered mixture of cation and anion exchange resins, corn starch, trolamine, and the like. Further, other potential materials are Category II actives as defined by the U.S. Food and Drug Administration's Tentative Final Monograph on Skin Protectant Drug Products for Over-the-Counter Human Use (21 C.F.R. § 347), which include: bismuth subnitrate, boric acid, ferric chloride, polyvinyl pyrrolidone-vinyl acetate copolymers, sulfur, tannic acid, and the like. The skin agent may be selected from these materials and mixtures thereof. As mentioned above, the materials for use should be safe. The rheological solid shave composition may include between about 0.001 wt. % and about 20 wt. %, by weight of the rheological solid shave composition, of the skin agent. The concentration range of the skin agents in the composition varies from material to material.

Compositions may also include one or more anti-fungal or anti-microbial actives such as metal pyrithione salt actives such as zinc pyrithione. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Surfactant

The composition may contain surfactant. Suitable surfactants include anionic surfactants, non-ionic surfactant, cationic surfactants, zwitterionic surfactants and amphoteric surfactants and mixtures thereof. Suitable surfactants may be linear or branched, substituted or un-substituted, and may be derived from petrochemical material or biomaterial.

Anionic surfactant: Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate. Usually, the hydrophobic group will comprise a C8-C22 alkyl, or acyl group. Such surfactants may be employed in the form of salts and the salt-forming cation usually is selected from sodium, potassium, ammonium, magnesium and the like with the sodium cation being the usual one chosen.

Anionic surfactants of the present invention and adjunct anionic cosurfactants, may exist in an acid form, and said acid form may be neutralized to form a surfactant salt which is desirable for use in the present compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, oligamines, or alkanolamines. Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Suitable sulphonate surfactants include methyl ester sulphonates, alpha olefin sulphonates, alkyl benzene sulphonates, especially alkyl benzene sulphonates, preferably C10-13 alkyl benzene sulphonate. Suitable alkyl benzene sulphonate (LAS) is obtainable, preferably obtained, by sulphonating commercially available linear alkyl benzene (LAB). Suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulphonate that is obtained by DETAL catalyzed process, although other synthesis routes, such as HF, may also be suitable. In one aspect a magnesium salt of LAS is used Suitable sulphate surfactants include alkyl sulphate, preferably $C_{8-18}$ alkyl sulphate, or predominantly $C_{12}$ alkyl sulphate.

Other suitable anionic surfactants include alkyl ether carboxylates.

Suitable non-ionic surfactants are selected from the group consisting of: $C_8$-$C_{18}$ alkyl ethoxylates, such as, NEODOL® non-ionic surfactants from Shell; $C_6$-$C_{12}$ alkyl phenol alkoxylates wherein preferably the alkoxylate units are ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; alkylpolysaccharides, preferably alkylpolyglycosides; methyl ester ethoxylates; polyhydroxy fatty acid amides; ether capped poly(oxyalkylated) alcohol surfactants; and mixtures thereof.

Suitable non-ionic surfactants include alkylpolyglucoside and/or an alkyl alkoxylated alcohol.

Suitable non-ionic surfactants include alkyl alkoxylated alcohols, preferably $C_{8-18}$ alkyl alkoxylated alcohol, preferably a $C_{8-18}$ alkyl ethoxylated alcohol, preferably the alkyl alkoxylated alcohol has an average degree of alkoxylation of from 1 to 50, preferably from 1 to 30, or from 1 to 20, or from 1 to 10, preferably the alkyl alkoxylated alcohol is a $C_{8-18}$ alkyl ethoxylated alcohol having an average degree of ethoxylation of from 1 to 10, preferably from 1 to 7, more preferably from 1 to 5 and most preferably from 3 to 7. The alkyl alkoxylated alcohol can be linear or branched, and substituted or un-substituted. Suitable nonionic surfactants include those with the trade name Lutensol® from BASF.

Suitable cationic surfactants include alkyl pyridinium compounds, alkyl quaternary ammonium compounds, alkyl quaternary phosphonium compounds, alkyl ternary sulphonium compounds, and mixtures thereof.

Cationic surfactants include quaternary ammonium compounds having the general formula:

$$(R)(R_1)(R_2)(R_3)N^+X^-$$

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, preferred anions include: halides, preferably chloride; sulphate; and sulphonate.

Suitable amphoteric or zwitterionic surfactants include amine oxides, and/or betaines.

Exemplary amine oxides include alkyl dimethyl amine oxide or alkyl amido propyl dimethyl amine oxide, alkyl dimethyl amine oxide and coco dimethyl amino oxide. Amine oxides may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3) O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides.

Other suitable surfactants include betaines, such as alkyl betaines, alkylamidobetaine, amidazoliniumbetaine, sulfobetaine (INCI Sultaines) as well as Phosphobetaines Preservatives In embodiments, soluble active agent can include a preservative. The preservative may be present in an amount sufficient to prevent spoilage or prevent growth of inadvertently added microorganisms for a specific period of time, but not sufficient enough to contribute to the odor neutralizing performance of the rheological solid composition. In other words, the preservative is not being used as the antimicrobial compound to kill microorganisms on the surface onto which the rheological solid composition is deposited in order to eliminate odors produced by microorganisms. Instead, it is being used to prevent spoilage of the rheological solid composition in order to increase the shelf-life of the rheological solid composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation; 1,2-Benzisothiazolin-3-one; Acticide MBS.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the rheological solid composition.

Adjuvants

Adjuvants can be added to the rheological solid shave composition herein for their known purposes. Such adjuvants include, but are not limited to, water soluble metallic salts, including zinc salts, copper salts, and mixtures thereof; antistatic agents; insect and moth repelling agents; colorants; antioxidants; aromatherapy agents, non-encapsulated pigments, film forming agents, dispersants, antioxidants, essential oils, preserving agents, fragrances, liposoluble polymers that are dispersible in the medium, fillers, neutralizing agents, silicone elastomers, cosmetic and dermatological oil-soluble active agents such as, for example, emollients, moisturizers, vitamins, anti-wrinkle agents, essential fatty acids, sunscreens, and mixtures thereof can be added.

Water Soluble Metallic Salts

Sodium chloride (and other sodium salts) is a particular useful additive to the aqueous phase to adjust the thermal stability of compositions, but must be added into the composition with particular care (Example 3). Not wishing to be bound by theory, sodium chloride is thought to 'salt out' inventive crystallizing agents decreasing their solubility. This has the effect of increasing the thermal stability temperature of the rheological solid composition as measured by the THERMAL STABILITY TEST METHOD. For example, Optimal Chain Length crystallizing agents can have the thermal stability temperatures increased as much as 15° C. with sodium chloride addition. This is particularly valuable as the addition of other ingredients into the aqueous phase often lower the thermal stability temperature in the absence of sodium chloride. Surprisingly, adding sodium chloride can lead to adverse effects in the preparation of the rheological solid compositions. It is preferable in most making processes, to add sodium chloride into the hot crystallizing agent aqueous phase before cooling to form the mesh. However, adding too much may cause 'curding' of the crystallizing agents and absolutely horrid compositions. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the crystallizing agents, to form plates or platelet crystals, which are not rheological solids.

Antimicrobial Compounds

In embodiments, soluble active agent can include an effective amount of a compound for reducing the number of viable microbes in the air or on surfaces. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. The antimicrobial compounds may also be effective at reducing the number of viable viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the rheological solid composition can be water-soluble, Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

A quaternary compound may be used. Examples of commercially available quaternary compounds suitable for use in the rheological solid composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the rheological solid composition.

Vitamins

As used herein, "xanthine compound" means one or more xanthines, derivatives thereof, and mixtures thereof. Xanthine Compounds that can be useful herein include, but are not limited to, caffeine, xanthine, 1-methyl xanthine, theophylline, theobromine, derivatives thereof, and mixtures thereof. Among these compounds, caffeine is preferred in view of its solubility in the composition. The composition can contain from about 0.05%, preferably from about 2.0%, more preferably from about 0.1%, still more preferably from about 1.0%, and to about 0.2%, preferably to about 1.0%, more preferably to about 0.3% by weight of a xanthine compound As used herein, "vitamin B3 compound" means a one or more compounds having the formula:

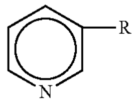

wherein R is CON niacinamide), —COOH (i.e., nicotinic acid) or $CH_2OH$ (i.e., nicotinyl alcohol); derivatives thereof; mixtures thereof; and salts of any of the foregoing.

Exemplary derivatives of the foregoing vitamin B3 compounds include nicotinic acid esters, including non-vasodilating esters of nicotinic acid (e.g, tocopherol nicotinate, and myristyl nicotinate), nicotinyl amino acids, nicotinyl alcohol esters of carboxylic acids, nicotinic acid N-oxide and niacinamide N-oxide. The composition can contain from about 0.05%, preferably from about 2.0%, more preferably from about 0.1%, still more preferably from about LO %, and to about 0 preferably to about 0.5%, more preferably to about 0.3% by weight of a vitamin B3 compound As used herein, the term "panthenol compound" is broad enough to include panthenol, one or more pantothenic acid derivatives, and mixtures thereof. panthenol and its derivatives can include D-panthenol ([R]-2,4-dihydroxy-N-[3-hydroxypropyl)]-3,3-dimethylbutamide), DL-panthenol, pantothenic acids and their salts, preferably the calcium salt, panthenyl triacetate, royal jelly, panthetine, pantotheine, panthenyl ethyl ether, pangamic acid, pantoyl lactose, vitamin B complex, or mixtures thereof. The composition can contain from about 0.01%, preferably from about 0.02%, more preferably from about 0.05%, and to about 3%, preferably to about 1%, more preferably to about 0.5% by weight of a panthenol compound Hair Removal Device The rheological solid shave composition may be used with a hair removal device. The rheological solid shave composition may be on-board the hair removal device such as in the form of a lubri-strip or wing. The rheological solid shave composition may be off-board the hair removal device. The rheological solid shave composition may be used together with the hair removal device such as before, during or after use of the hair removal device. The rheological solid shave composition may be available, such as commercially available, with the hair removal device such as in the form of a kit.

Hair Removal Device

According to some examples of the disclosure, the shaving aid finds particular application for hair removal devices. Hair removal devices generally comprise a hair removal head and a handle 30 and/or grip portion, upon which the hair removal head is mounted, either permanently or detachably/attachably. The hair removal device can be manual or power driven and can be used for wet and/or dry application. In some examples, the hair removal head may include a depilator, a dry shaver or an intense pulsed light device. In other examples, with reference to FIG. 1, the hair removal head may be a razor cartridge 10.

The hair removal head may be pivotally connected to a connecting structure 50 that in turn, or independently (e.g. permanently fixed), is connected to a handle 30. In some examples, the connecting structure 50 includes at least one arm 32 to releasably engage the hair removal head. The hair removal head may be integral with the handle 30 so that the hair removal device is discarded as a whole unit, or may comprise a detachable hair removal head that forms part of a shaving system, in which the detachable hair removal head is uncoupled from the handle 30 and disposed of and a new detachable hair removal head is coupled to the same handle.

The hair removal head typically comprises one or more elongated edges usually positioned between a first and second end, the one or more elongated edges comprising a tip extending forwardly. With reference to FIG. 1, where the hair removal head is a razor cartridge 10, the cartridge 10 may comprise a housing 12, and the one or more elongated edges can include one or more razor blades 20 incorporated into the housing 12, in which each blade 20 includes a blade edge 22.

A variety of razor cartridges can be used in accordance with the present disclosure. For example, U.S. Pat. No. 7,168,173 generally describes a FUSION® razor that is commercially available from The Gillette Company and which includes a razor cartridge with multiple blades. Non limiting examples of suitable razor cartridges, with and without fins, guards, and/or shave aids, include those marketed by The Gillette Company under the FUSION®, VENUS® product lines (Gillette) as well as those disclosed in U.S. Pat. Nos. 7,197,825, 6,449,849, 6,442,839, 6,301,785, 6,298,558, 6,161,288, and U.S. Patent Application Publication No. 2008/060201. Those of skill in the art will understand that the shaving aid can be used with any currently marketed razor or shaving system, including those having 2, 3, 4 or more blades. In such a case, the hair removal device is a razor, the hair removal head is a razor cartridge 10, and the one or more elongated edges are blades.

In some examples, at least one shaving aid such as the rheological solid of the present invention is located on a portion of the cartridge 10 that contacts skin during the hair removal process, forward and/or aft of the blades 20. A feature "forward" of the one or more elongated edges, for example, is positioned so that the surface to be treated by the hair removal device encounters the feature before it encounters the elongated edges. A feature "aft" of the elongated edge is positioned so that the surface to be treated by the hair removal device encounters the feature after it encounters the elongated edges.

In the example shown in FIG. 1, a shaving aid 18 is positioned on a cap 16 of the razor cartridge 10. In other examples, a plurality of shaving aids may be provided on the hair removal head, in which the plurality of shaving aids may be the same (identical) or different in terms of physical shape/structure and/or chemical composition. For example, one of the plurality of shaving aids may be a rheological solid of the present invention while another of the shaving aids may be a conventional lubri-strip or wing. These shaving aids may be placed collectively (for example adjacent to one another) ahead of or behind the elongated edges (e.g. blades on a razor cartridge), including side by side, or separately with one ahead of the elongated edges and the other behind.

The shaving aid may be separate from or attached to the hair removal device or head. The shaving aid may be attached to the hair removal device or head by any suitable attachment means such as adhesive or interference fit or may be contained at least partially within a container 40. Exemplary embodiments of solid shaving aids contained in containers include US2011/0041865 and US2012/0023763. The shaving aid may be formed in the container 40 by any means. The shaving aid may be formulated directly in the container 40 such as by molding directly into the container.

In some examples, as shown in FIG. 1, the cartridge 10 comprises a guard 14 comprising at least one elongated flexible protrusion (not labeled) to engage a user's skin. The at least one flexible protrusion may comprise flexible fins generally parallel to the one or more elongated edges. The at least one flexible protrusion may additionally or alternatively comprise flexible fins comprising at least one portion which is not generally parallel to the one or more elongated edges. Non-limiting examples of suitable guards include those used in current razor blades and include those disclosed in U.S. Pat. Nos. 7,607,230 and 7,024,776; (disclosing elastomeric/flexible fin bars); and U.S. Patent Application Publication Nos. 2008/0034590 (disclosing curved guard fins) and 2009/0049695A1 (disclosing an elastomeric guard having guard forming at least one passage extending between an upper surface and a lower surface). In some examples, the shaving aid is positioned on the cartridge 10 aft of the guard and forward of the elongated edge. In another example, the shaving aid such as the rheological solid of the present invention is positioned on the cartridge 10 forward of the guard. This example can be particularly useful to deliver the shaving aid prior to contact with the guard.

Figure 6A:
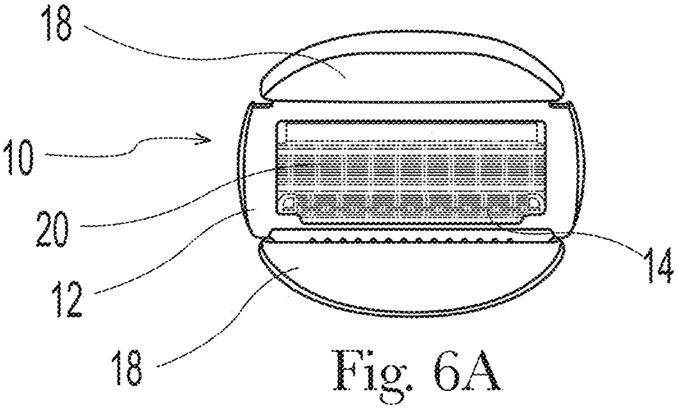
FIG. 6A. is a front view of a razor cartridge comprising a rheological solid composition as a shaving aid in the form of wings in accordance with the present disclosure FIG. 6B. is A side view of a razor cartridge comprising a rheological solid composition as a shaving aid in the form of wings in accordance with the present disclosure FIG. 6C. is a perspective view of a razor cartridge comprising a rheological solid composition as a shaving aid in the form of wings in accordance with the present disclosure FIG. 7. is an exploded view of a razor comprising a rheological solid composition as a shaving aid in the form of wings and separate housings for the blades and the shaving aid.
Figure 6B:
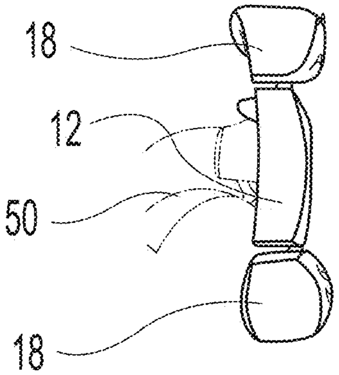
Figure 6C:
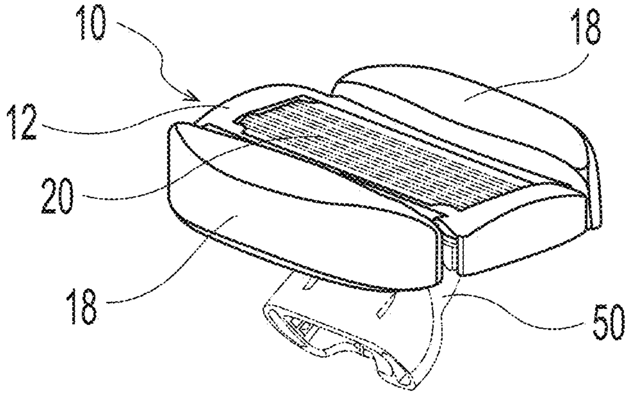

The shaving aid 18 on-board the hair removal device, such as a shaving aid comprising the rheological solid of the present invention, may take the form of wings, which are generally disposed on the hair removal head, generally outward of housing 12. Wings may be disposed forward or aft of the housing 12. Alternately or additionally, the wings may be disposed on the sides of the housing. FIGS. 6*a*, 6*b* and 6*c* depict a top view, side view and oblique view (respectively) of a hair removal head with wings.

Figure 7:
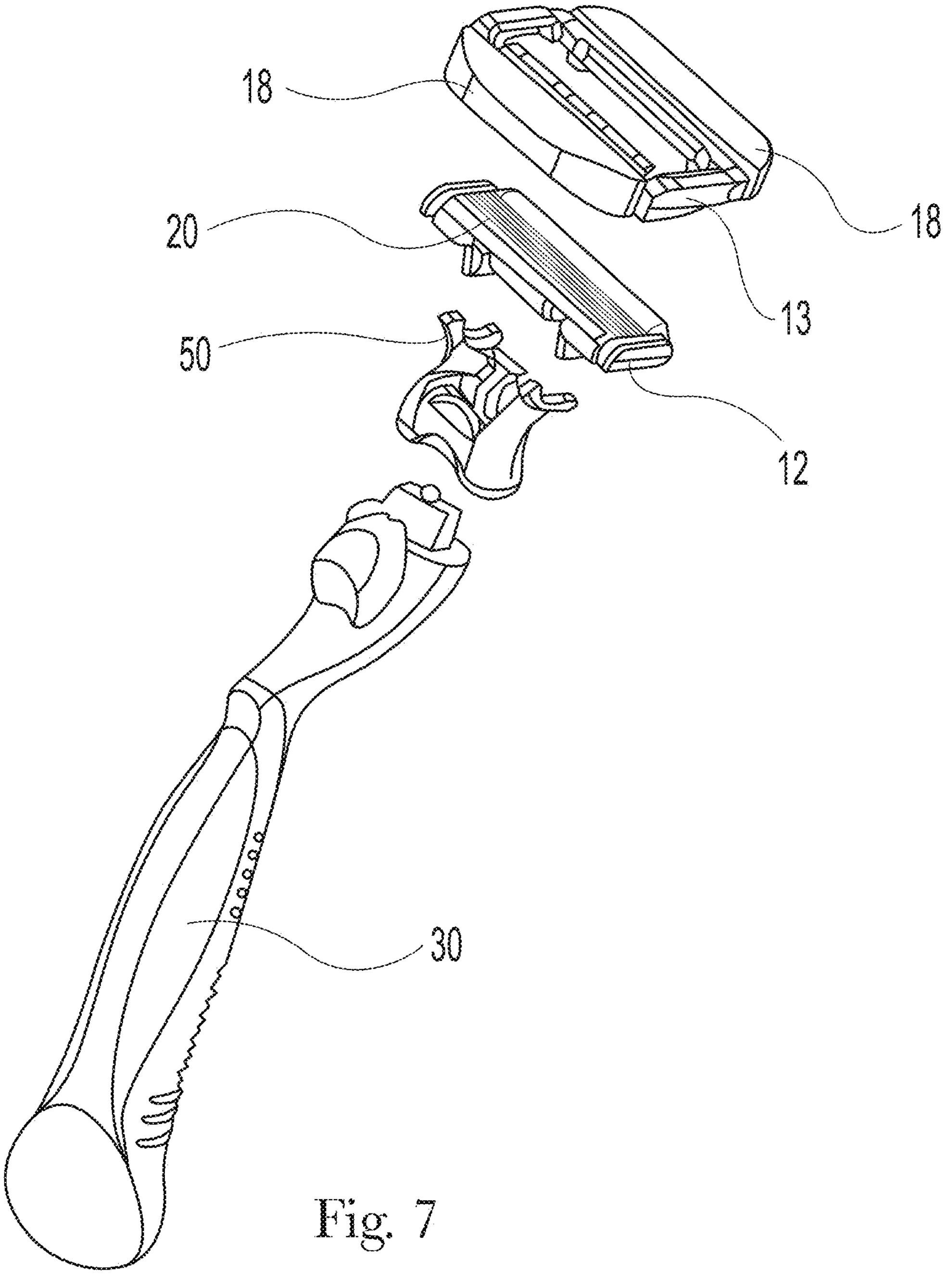

The shaving aid 18 such as a shaving aid in the form of wings may be integral with the housing 12 containing the at least one elongated edge such as a blade 20 or may be incorporated into a separate housing 13. FIG. 7 depicts an exploded view of a razor comprising separate housings for the blades 20 and the shaving aid 18.

Figure 8A:
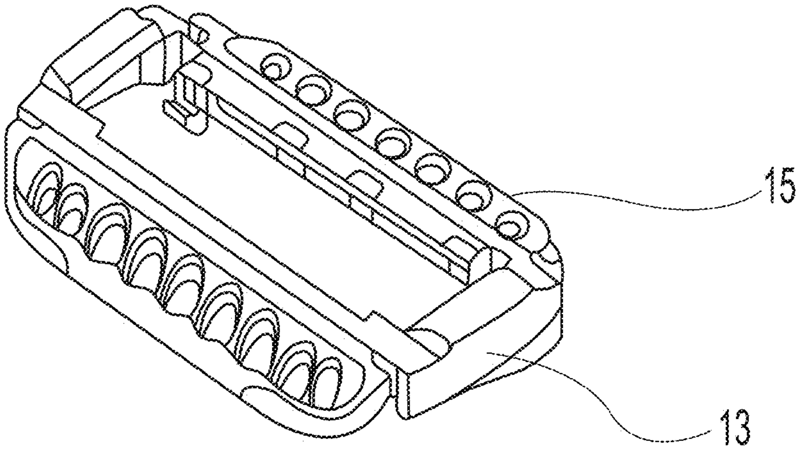
FIG. 8A. is a perspective view of a housing comprising a protrusion comprising voids for attachment of the rheological solid to the housing.
Figure 8B:
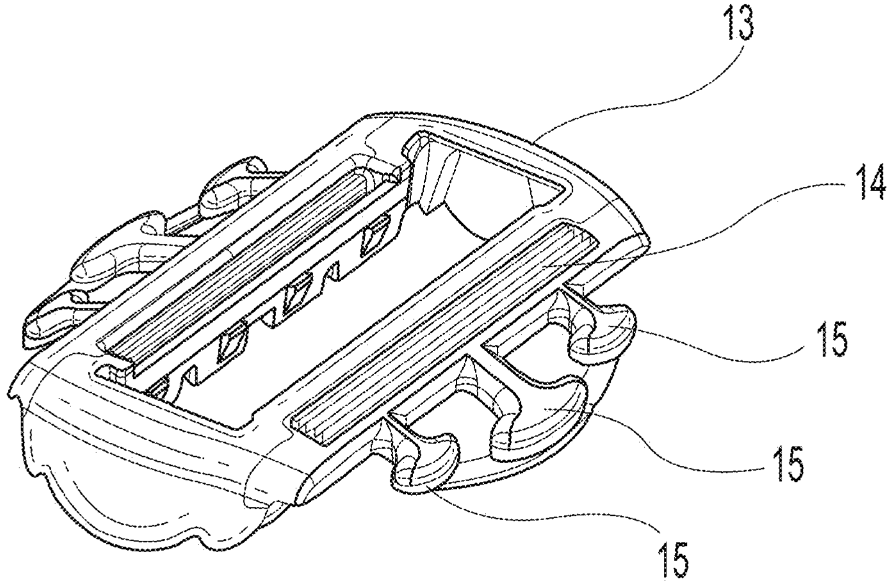
FIG. 8B. is a perspective view of a housing comprising a protrusion comprising undercuts for attachment of the rheological solid to the housing.

The shaving aid 18 such as a shaving aid in the form of wings may be attached to the housing 12 (not shown) or the housing 13 by any means. The wings may be over-molded onto one or more protrusions 15 from the housing. The protrusions that incorporate voids such as cut-outs or undercuts to allow the shaving aid to be retained onto the housing. FIGS. 8*a* and 8*b* depict protrusion comprising voids and undercuts, respectively.

Rheological Solid Composition Properties

Such compositions exhibit three properties used to make effective consumer product for envisioned applications:

Aqueous Phase Expression

Aqueous phase expression is an important property for consumer applications in the present invention, expressed in work to express water per unit volume, where preferred compositions are between 300 J m-3 and about 9,000 J m-3, more preferably between 1,000 J m-3 and about 8,000 J m-3, more preferably between 2,000 J m-3 and about 7,000 J m-3 and most preferably between 2,500 J m-3 and about 6,000 J m-3, as determined by the AQUEOUS PHASE EXPRESSION TEST METHOD. These limits allow for viable product compositions that—for example, provide evaporative and/or sensate-based cooling when the composition is applied to the skin and cleaning when applied to a hard surface. These work limits are in contrast to bar soaps and deodorant sticks that do not express aqueous phase when compressed. These work limits are also in contrast to gelatins that likewise do not express water when compressed. So, it is surprising that high-water compositions can be created with these materials, that express aqueous phase with compression. Not wishing to be bound by theory, it is believed this a result of a network of crystalline materials that break up during the application of sufficient stress—releasing the aqueous phase with no uptake when the compression is released.

Firmness

Firmness should be agreeable to consumer applications, in forming a structured rheological solid composition, with preferred embodiments between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as a rheological solid stick to provide a dry-to-the-touch but wet-to-the-push properties. The firmness values are significantly softer than bar soaps and deodorants, which exceed these values. So, it is surprising that high-water compositions can be created that remain as rheological solid compositions with between about 0.25 wt % to about 10 wt % crystallizing agent, more preferably between about 0.5 wt % to about 7 wt % crystallizing agent and most preferably between about 1 wt % to about 5 wt % crystallizing agent. Not wishing to be bound by theory, it is believed this a result of crystallizing agent materials creating the interlocking mesh that provides sufficient firmness.

Thermal Stability

Thermal stability is used to ensure that the structured rheological solid composition can be delivered as intended to the consumer through the supply chain, preferably with thermal stability greater than about 40° C., more preferably greater than about 45° C. and most preferably greater than about 50° C., as determined by the THERMAL STABILITY TEST METHOD. Creating compositions with acceptable thermal stability is difficult, as it may vary unpredictably with concentration of the crystallizing agent and soluble active agent(s). Not wishing to be bound by theory, thermal stability results from the insolubility of the crystallizing agent in the aqueous phase. Conversely, thermal instability is thought to result from complete solubilization of the crystallizing agent that comprised the mesh.

Stability Temperature

Stability temperature, as used herein, is the temperature at which most or all of the crystallizing agent completely dissolves into an aqueous phase, such that a composition no longer exhibits a stable solid structure and may be considered a liquid. In embodiments of the present invention the stability temperature range may be from about 40° C. to about 95° C., about 40° C. to about 90° C., about 50° C. to about 80° C., or from about 60° C. to about 70° C., as these temperatures are typical in a supply chain. Stability temperature can be determined using the THERMAL STABILITY TEST METHOD, as described below.

Firmness

Depending on the intended application, such as a stick, firmness of the composition may also be considered. The firmness of a composition may, for example, be expressed in Newtons of force. For example, compositions of the present invention comprising 1-3 wt % crystallizing agent may give values of about 4-about 12 N, in the form of a solid stick or coating on a sheet. As is evident, the firmness of the composition according to embodiments of the present invention may, for example, be such that the composition is advantageously self-supporting and can release liquids and/or actives upon application of low to moderate force, for example upon contact with a surface, to form a satisfactory deposit on a surface, such as the skin and/or superficial body growths, such as keratinous fibers. In addition, this hardness may impart good impact strength to the inventive compositions, which may be molded or cast, for example, into stick or sheet form, such as a wipe or dryer sheet product. The composition of the invention may also be transparent or clear, including for example, a composition without pigments. Preferred firmness is between about 0.1 N to about 50.0 N, more preferably between about 0.5 N to about 40.0 N, more preferably between about 1.0 N to about 30.0 N and most preferably between about 2.5 N to about 15.0 N. The firmness may be measured using the FIRMNESS TEST METHOD, as described below.

Aqueous Phase Expression

Depending on the intended application, such as a stick, aqueous phase expression of the composition may also be considered. This is a measure of the amount of work need per unit volume to express the aqueous phase from the compositions, with larger values meaning it becomes more difficult to express liquid. A low value might be preferred, for example, when applying the composition to the skin. A high value might be preferred, for example, when the composition is applied to a substrate that requires 'dry-to-the-touch-but-wet-to-the-wipe' properties. Preferred values are between about 100 J m-3 to about 8,000 J m-3, more preferably between about 1,000 J m-3 to about 7,000 J m-3, and most preferably between about 2,000 J m-3 to about 5,000 J m-3. The liquid expression may be measured using the AQUEOUS PHASE EXPRESSION TEST METHOD, as described herein.

Firmness Test Method

All samples and procedures are maintained at room temperature (25±3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-position so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD, are all entered in the examples in the row entitles 'Firmness'. In general, the numeric value is returned as the average of the maximum value of three measurements as described above, except in one of the two cases:

1) the composition does not form a homogenous rheological solid (e.g. completely or partially liquid), the value of 'NM1' is returned;
2) and, the composition curds during making, the value of 'NM2' is returned.

Thermal Stability Test Method

All samples and procedures are maintained at room temperature (25±3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent; Mettler Toledo, LLC., Columbus, OH). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC (TA Instruments, New Castle, DE) in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD, are all entered in the examples in the row entitles 'Temperature'. In general, the numeric value is returned as described above, except in one of the two cases:

1) the composition does not form a homogenous rheological solid (e.g. completely or partially liquid) and is not suitable for the measurement, the value of 'NM3' is returned;
2) and, the composition curds during making and is not suitable for the measurement, the value of 'NM4' is returned.

Aqueous Phase Expression Test Method

All samples and procedures are maintained at room temperature 25 (±3° C.) prior to testing.

Measurements for the determination of aqueous phase expression were made with a TA Discovery HR-2 Hybrid Rheometer (TA Instruments, New Castle, DE) and accompanying TRIOS software version 3.2.0.3877, or equivalent. The instrument is outfitted with a DHR Immobilization Cell (TA Instrument) and 55 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. It is critical that the sample be prepared in Speed Mixer containers (Flak-Tech, Max 60 Cup Translucent, Cat #501 222t), so that the diameter of the sample matches the diameter of the HR-2 Immobilization Cell. The sample is released from the containers by running a thin spatula between the edge of the container and the sample. The container is gently turned over and placed on a flat surface. A gentle force is applied to the center of the bottom of the overturned container, until the sample releases and gently glides out of the container. The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the aqueous phase to escape through the bottom of the sample. This also ensures that any change in the height of the sample for the experiment is equivalent to the amount of aqueous phase expressed during the test. At the end of the measurement, one should confirm that the aqueous phase is indeed expressed from the sample through the measurement, by looking for aqueous phase in the effluent tube connected to the Immobilization Cell. If no aqueous phase is observed, the sample is deemed not to express aqueous phase and is not inventive.

Set the instrument settings as follows. Select Axial Test Geometry. Then, set "Geometry" options: Diameter=50 mm; Gap=45000 um; Loading Gap=45000 um; Trim Gap Offset=50 um; Material='Steel'; Environmental System="Peltier Plate". Set "Procedure" options: Temperature=25° C.; Soak Time=0 sec; Duration=2000 sec; Motor Direction="Compression"; Constant Linear Rate=2 um sec-1; Maximum Gap Change=0 um; Torque=0 uN·m; Data Acquisition='save image' every 5 sec.

Manually move the steel tool within about 1000 um of the surface of the sample, taking care that the tool does not touch the surface. In the "Geometry" options, reset Gap to this distance.

Start the run.

The data is expressed in two plots:

1) Plot 1: Axial Force (N) on the left-y-axis and Step Time (s) on the x-axis;

2) Plot 2: Gap (um) on the right-y-axis and Step Time (s) on the x-axis.

The Contact Time—T(contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the aqueous phase from the structure is the area under the Axial Force curve in Plot 1 between T(contact) and T(compression) multiplied by Constant Linear Rate, or 2e-6 m s-1 normalized by dividing the total volume of expressed fluids, and is expressed in units of Joules per cubic meter (J m-3).

The results of the AQUEOUS PHASE EXPRESSION TEST METHOD, are all entered in the examples in the row entitled 'AP Expression'. In general, the numeric value, as the average of at least two values is returned as described, except in one of the three cases:

1) the composition does not form a homogenous rheological solid (e.g. completely or partially liquid) and is not suitable for the measurement, the value of 'NM5' is returned;
2) the composition curds during making and is not suitable for the measurement, the value of 'NM6' is returned;
3) the composition is a rheological solid but too soft to effectively load in the device, the value of 'NM7' is returned;
4) and the composition is too hard so that the force exceeds 50 N before the 15% compression, the value of 'NM8' is returned;

Blend Test Method

All samples and procedures are maintained at room temperature 25 (±3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent. A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hot plate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, CA), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250 C for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the crystallizing agent is described in the following ways:

Optimal Purity—Po, which is the mass fraction of the optimal chain length molecules in the crystallizing agent blend calculated as:

$$Po = \frac{\sum Mo}{Mt}$$

where Mo is the mass of each optimal chain length in the crystallizing agent and Mt is the total mass of the crystallizing agent.

Single Purity—Ps, which is the mass fraction of the most common chain length in the crystallizing agent blend calculated as:

$$Ps = \frac{Ms}{Mt}$$

where Ms is the mass of the most common chain length in the crystallizing agent and Mt is the total mass of the crystallizing agent. The value is expressed in brackets—[Ms], if the most common chain length is selected from the group of unsuitable chain length molecules.

EXAMPLES

Materials List (1) Water: Millipore, Burlington, MA (18 m-ohm resistance)

(2) Sodium caprate (sodium decanoate, NaC10): TCI Chemicals, Cat #D0024

(3) Sodium laurate (sodium dodecanoate, NaC12): TCI Chemicals, Cat #D0024

(4) Sodium myristate (sodium tetradecanoate, NaC14): TCI Chemicals, Cat. #M0483

(5) Sodium palmitate (sodium hexadecanoate, NaC16): TCI Chemicals, Cat. #P0007

(6) Sodium stearate (sodium octadecanoate, NaC18): TCI Chemicals, Cat. #S0081

(7) Sodium oleate (sodium trans-9-octadecanoate, NaC18:1): TCI Chemicals, Cat #O0057

(8) Pentadecylic acid (pentadecanoic acid, HC15): TCI Chemicals, Cat #P0035

(9) Margaric acid (heptadecanoic acid, HC17): TCI Chemicals, Cat #H0019

(10) Nonadecylic acid (nonadecanoic acid, HC19): TCI Chemicals, Cat #N0283

(11) C1270 K ID: P&G Chemicals, Cincinnati, OH) prod. code 10275803

(12) C1618 K ID: P&G Chemicals, Cincinnati, OH) prod. code 10275805

(13) C1218 K ID: P&G Chemicals, Cincinnati, OH) prod. code 10275798

(14) C1214 K ID: P&G Chemicals, Cincinnati, OH) prod. code 10275796

(15) NaOH: 0.10 M, Fluka Chemical, Cat #319481-500ML

(16) Sodium chloride (NaCl): VWR, Cat #BDH9286-500G

(17) Lauric acid (HL): TCI Chemicals, Cat #L0011

(18) NaOH: 1.0 N, Honeywell/Fluka, Cat #35256-1L

Example 1

These include samples containing crystallizing agents with a Po value of about 1 and Ps value of also about 1, as determined by the BLEND TEST METHOD, contrasting optimal and unsuitable crystallizing agents. Examples A-E (Tables 1-2) show samples prepared with different weight percentage of sodium tetradecanoate. The increasing concentrations increase both firmness and temperature stability of the samples, but also make it more difficult to express aqueous phase, as reflected in the aqueous phase expression value. As Example E shows—at about 9 wt %, it is no longer practical to express aqueous phase, as has been observed with soap bars that use these materials as gelling agents. Examples F-H (Table 2), show that other optimal chain length crystallizing agents, share similar trends as the previous examples. Example I-K (Table 3) have unsuitable crystallizing agents, and the sample compositions result in liquids. Not wishing to be bound by theory, it is believed these crystallizing agents are either too soluble (e.g. low Krafft Temperature) or 'kinks' from unsaturation in the chains disrupts crystallization. Examples L-N (Table 4) demonstrate that it is possible to create compositions with odd-chain length crystallizing agents. It is believed odd-chain-length crystallizing agents crystallize in a different manner than even chain-length crystallizing agents, so that it is surprising these compositions still form effective mesh structures.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples A-K were prepared by first adding Water (1) and crystallizing agent (2-7) to the beaker. The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples. Representative data demonstrates that the prototypes exhibit the required properties for these rheological solid compositions.

Examples L-N were prepared by first adding NaOH (15) and fatty acid (8-10) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml. The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples and blend was determined from the BLEND TEST METHOD. Representative data demonstrates that the prototypes exhibit the required properties of firmness, aqueous phase expression and thermal stability for these rheological solid compositions.

TABLE 1

| | Sample A FG4005-7 Inventive | Sample B FG4005-8 Inventive | Sample C FG4005-9 Inventive | Sample D FG4005-10 Inventive |
|---|---|---|---|---|
| (1) Water | 99.501 g | 99.001 g | 97.001 g | 95.001 g |
| (2) NaC10 | — | — | — | — |
| (3) NaC12 | — | — | — | — |
| (4) NaC14 | 0.500 g | 1.003 g | 3.001 g | 5.003 g |
| (5) NaC16 | — | — | — | — |
| (6) NaC18 | — | — | — | — |
| (7) NaC18:1 | — | — | — | — |
| % Crystallizing Agent | 0.5 wt % | 1.0 wt % | 3.0 wt % | 5.0 wt % |
| Firmness | 0.51N | 1.24N | 8.65N | 14.31N |
| AP Expression | NM7 | 340 J m−3 | 6,260 J m−3 | 7.730 J m−3 |
| Temperature | 46.7° C. | 45.0° C. | 48.5° C. | 54.3° C. |
| Po | 1.00 | 1.00 | 1.00 | 1.00 |
| Ps | 1.00 | 1.00 | 1.00 | 1.00 |

TABLE 2

| | Sample E FG4005-12 Comparative | Sample F FG4005-13 Inventive | Sample G FG4005-17 Inventive | Sample H FG4005-23 Inventive |
|---|---|---|---|---|
| (1) Water | 91.000 g | 99.501 g | 93.002 g | 93.002 g |
| (2) NaC10 | | — | — | — |
| (3) NaC12 | — | — | — | — |
| (4) NaC14 | 9.000 g | — | — | — |
| (5) NaC16 | — | 0.500 g | 7.002 g | — |
| (6) NaC18 | — | — | — | 7.000 g |
| (7) NaC18:l | — | — | — | — |
| % Crystallizing Agent | 9.0 wt % | 0.5 wt % | 7.0 wt % | 7.0 wt % |
| Firmness | 40.92N | 0.51N | 5.03N | 4.19N |
| AP Expression | NM8 | NM7 | 2,550 J m−3 | 4,230 J m−3 |
| Temperature | 56.4° C. | 59.0° C. | 64.3° C. | 78.0° C. |
| Po | 1.00 | 1.00 | 1.00 | 1.00 |
| Ps | 1.00 | 1.00 | 1.00 | 1.00 |

TABLE 3

| | Sample I NB Comparative | Sample J 1531-32 Comparative | Sample K 1531-33 Comparative |
|---|---|---|---|
| (1) Water | 48.500 g | 48.611 g | 48.740 g |
| (2) NaC10 | 1.500 g | — | — |
| (3) NaC12 | — | 1.547 g | — |
| (4) NaC14 | — | — | — |
| (5) NaC16 | — | — | — |
| (6) NaC18 | — | — | — |
| (7) NaC18:1 | — | — | 1.505 g |
| % Crystallizing Agent | 3.0 wt % | 3.1 wt % | 3.0 wt % |
| Firmness | NM1 | NM1 | NM1 |
| AP Expression | NM5 | NM5 | NM5 |
| Temperature | NM3 | NM3 | NM3 |
| Po | 0.00 | 0.00 | 0.00 |
| Ps | [1.00] | [1.00] | [1.00] |

TABLE 4

| | Sample L 1531-100 Inventive | Sample M 1531-101 Inventive | Sample N 1531-102 Inventive |
|---|---|---|---|
| (8) H C15 | — | 2.561 g | — |
| (9) H C17 | 2.761 g | — | — |
| (10) H C19 | — | — | 3.090 g |
| % Crystallizing Agent | 2.76 wt % | 2.56 wt % | 3.09 wt % |
| (15) NaOH | 97.210 g | 97.442 g | 96.911 g |
| Firmness | 8.10N | 4.49N | 4.77N |
| AP Expression | 6,001 J m−3 | 3,688 J m−3 | 3,327 J m−3 |
| Temperature | 75.2° C. | 63.0° C. | 83.3° C. |
| Po | 1.00 | 1.00 | 1.00 |
| Ps | 1.00 | 1.00 | 1.00 |

Example 2

This example includes compositions that contain blends of crystallizing agent molecules, as determined by the BLEND TEST METHOD, contrasting the effects of the relative amounts of optimal and unsuitable chain length crystallizing agent molecules on the three required properties. Examples O-R (Table 5) show samples prepared using different weight percentages of typical commercial fatty acid mixtures. The header shows the particular crystallizing agent used in the preparation and the 'from analysis' shows the chain length distribution from the BLEND TEST METHOD. All the compositions failed to crystallize and could not be measured for firmness, stability temperature or aqueous phase expression. Not wishing to be bound by theory, it is believed these samples have too high a level of unsuitable crystallizing agents to initiate viable mesh formation. Examples S-V (Table 6) show the effect of adjusting the comparative levels of optimal and unsuitable crystallizing agent chain length in the composition. While the weight percent of the crystallizing agent remains constant in the compositions, the amount of unsuitable chain length (C10) increases, resulting in the production of softer compositions having lower thermal stability temperature that do not crystallize to form a mesh structure. Examples W-Z (Table 7) show the effect of adjusting the comparative levels of optimal and unsuitable crystallizing agent chain length in the composition. While the weight percent of the crystallizing agent remains constant in the compositions, the amount of unsuitable chain length (C10) increases resulting in the production of softer compositions, having lower thermal stability temperature that do not crystallize to form a mesh structure. Surprisingly, the effect of the unsuitable crystallizing agents is more detrimental in combination with the shorter chain length optimal crystallizing agent. Not wishing to be bound by theory, but it is believed that the fibrous crystals are 'held' together primarily by chain-to-chain interactions of the crystallizing agents in the crystals and, being fewer with shorter chain length crystallizing agents, are more susceptible to the presence of unsuitable crystallizing agents in the crystals.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples O-R were prepared by first adding NaOH (15) and commercial fatty acid (11-14) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml. They were cooled at room temperature 25 (±3° C.). These samples remained liquid and consequently were not measured for firmness, thermal stability or water expression. One skilled in art recognizes that cooling compositions of crystallizing agent at different rates may result in modest differences in the firmness, aqueous phase expression and stability temperature properties; this is common in samples prepared at different absolute weights.

Examples S-Z were prepared by first adding Water (1) and crystallizing agent (2-7) to the beaker. The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Aqueous phase expression measurements were made by the AQUEOUS PHASE EXPRESSION TEST METHOD on the two 25 ml samples, in all cases except Example V and Example Z, which remained liquid. The blend was determined from the BLEND TEST METHOD.

One skilled in art recognizes that cooling compositions of crystallizing agent at different rates may result in modest differences in the firmness, aqueous phase expression and stability temperature properties; this is common in samples prepared at different absolute weights.

TABLE 5

| | Sample O 1531-119 (11) C-1270 K Comparative | Sample P 1531-120 (12) C-1618 K Comparative | Sample Q 1531-121 (13) C-1218 K Comparative | Sample R 1531-122 (14) C-1214 K Comparative |
|---|---|---|---|---|
| Wt. Crystallizing Agent | 1.504 g | 1.515 g | 1.509 g | 1.511 g |
| (1) Water | 41.607 g | 43.533 g | 42.195 g | 41.708 g |
| (18) NaOH | 6.963 g | 5.020 g | 6.435 g | 6.843 g |
| % Crystallizing Agent | 3.00 wt % | 3.03 wt % | 3.00 wt % | 3.02 wt % |
| Firmness | NM1 | NM1 | NM1 | NM1 |
| AP Expression | NM5 | NM5 | NM5 | NM5 |
| Temperature | NM3 | NM3 | NM3 | NM3 |
| Po | 0.26 | 0.25 | 0.27 | 0.28 |
| Ps | [0.74] | [0.69] | [0.58] | [0.72] |
| (Chain length distribution for each crystallizing agent) | | | | |
| HC8 | — | — | — | — |
| HC10 | — | — | — | — |
| HC12 | 1.113 g | — | 0.875 g | 1.088 g |
| HC13 | — | — | — | — |
| HC14 | 0.391 g | — | 0.287 g | 0.378 g |
| HC15 | — | — | — | — |
| HC16 | — | 0.300 g | 0.121 g | 0.045 g |
| HC17 | — | — | — | — |
| HC18 | — | 0.076 g | 0.226 g | — |
| HC18:1 | — | 1.045 g | — | — |
| Other | — | 0.106 g | — | — |

TABLE 6

| | Sample S FG4011-31 Inventive | Sample T FG4011-32 Inventive | Sample U FG4011-33 Inventive | Sample V FG4011-35 Comparative |
|---|---|---|---|---|
| (1) Water | 47.501 g | 47.501 g | 47.500 g | 47.501 g |
| (2) NaC10 | — | 0.500 g | 1.000 g | 2.000 g |
| (3) NaC12 | — | — | — | — |
| (4) NaC14 | 2.500 g | 2.000 g | 1.505 g | 0.501 g |
| (5) NaC16 | — | — | — | — |
| (6) NaC18 | — | — | — | — |
| (7) NaC18:1 | — | — | — | — |
| % Crystallizing Agent | 5.0 wt % | 5.0 wt % | 5.1 wt % | 5.0 wt % |
| Firmness | 16.2N | 13.7N | 11.7N | NM1 |
| AP Expression | 8,107 J m−3 | 8,753 J m−3 | 2,176 J m−3 | NM5 |
| Temperature | 48.6° C. | 44.5° C. | 40.0° C. | NM3 |
| Po | 1.00 | 0.80 | 0.60 | 0.20 |
| Ps | 1.00 | 0.80 | 0.60 | [0.8] |

TABLE 7

| | Sample W FG4011-43 Inventive | Sample X FG4011-44 Inventive | Sample Y FG4011-46 Inventive | Sample Z FG4011-78 Comparative |
|---|---|---|---|---|
| (1) Water | 47.502 g | 47.501 g | 47.502 g | 47.500 g |
| (2) NaC10 | — | 0.504 g | 1.500 g | 2.252 g |
| (3) NaC12 | — | — | — | — |
| (4) NaC14 | — | — | — | — |
| (5) NaC16 | — | — | — | — |
| (6) NaC18 | 2.500 g | 2.002 g | 1.003 g | 0.253 g |
| (7) NaC18:1 | — | — | — | — |
| % Crystallizing Agent | 5.0 wt % | 5.0 wt % | 5.0 wt % | 5.0 wt % |
| Firmness | 2.5N | 1.5N | 0.8N | NM1 |
| AP Expression | 4,560 J m−3 | 1,308 J m−3 | TBD | NM5 |
| Temperature | 73.0° C. | 72.6° C. | 60.6° C. | NM3 |
| Po | 1.00 | 0.80 | 0.60 | 0.10 |
| Ps | 1.00 | 0.80 | [0.60] | [0.90] |

Example 3

This include example demonstrates the effect of sodium chloride addition on the thermal stability and firmness of the rheological solid composition. Examples AA-AD (Table 8) show the effect of adding sodium chloride into the hot mixture of crystallizing agent and aqueous phase. Example AA is the control, without sodium chloride addition. Example AB and Example AC have increasing amounts of sodium chloride which results in increasing thermal stability temperature, but with a slight decrease in firmness. Surprisingly, Example AD curds the hot mixture. Not wishing to be bound by theory, but it is believed the sodium chloride is thought to 'salt out' the crystallizing agent so that it becomes soluble only at higher temperature; and also changes the crystallization of the crystallizing agent resulting in slightly softer compositions. However, when the sodium chloride level is too high, the solubility temperature exceeds the processing temperature and the mixtures curd. Once curding has occurred, it can no longer form the crystalline mesh. Examples AE-AG demonstrate a solution to this problem. In these examples, the crystalline mesh is formed first and then the sodium chloride is physically added to the top of the rheological solid composition. In this progression, the sodium chloride concentration increases the thermal stability temperature, while not changing the firmness. Not wishing to be bound by theory, it is believed that the crystalline mesh is formed as in the control Example AA, and that the added sodium chloride diffuses through the composition to change the solubility of the fibrous crystallizing agent, but not the nature of the fibers. Curding is no longer a problem, as the mixtures are crystallized first before the salt addition. This approach provides a more than 20-degree increase in the thermal stability temperature.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples AA-AD were prepared by adding Water (1), NaM (4) and sodium chloride (16) to the beaker. The beaker was placed on the heating-pad assembly. The overhead stirrer was placed in the beaker and set to rotate at 100 rpm. The heater was set at 80° C. The preparation was heated to 80° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. Firmness measurements were made with the FIRMNESS TEST METHOD, thermal stability measurement was made by the THERMAL STABILITY TEST METHOD and purity was determined from the BLEND TEST METHOD. Examples AE-AG were prepared by adding Water (1) and NaM (4) the beaker. The beaker was placed on the heating-pad assembly. The overhead stirrer was placed in the beaker and set to rotate at 100 rpm. The heater was set at 80° C. The preparation was heated to 80° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. The sodium chloride (16) was added to the top of the composition and allowed to diffuse through the composition for one week, before measurement. Firmness measurements were made with the FIRMNESS TEST METHOD, thermal stability measurement was made by the THERMAL STABILITY TEST METHOD and purity was determined from the BLEND TEST METHOD. One skilled in art recognizes that cooling compositions of crystallizing agent at different rates may result in modest differences in the firmness, aqueous phase expression and stability temperature properties; this is common in samples prepared at different absolute weights.

TABLE 8

| | Sample AA 1531-9 Inventive | Sample AB 1531-10 Inventive | Sample AC 1531-11 Inventive | Sample AD 1531-12 Comparative |
|---|---|---|---|---|
| (1) Water | 48.531 g | 48.070 g | 47.028 g | 43.742 g |
| (4) NaM | 1.519 g | 1.512 g | 1.478 g | 1.358 g |
| % Crystallizing Agent | 3.03 wt % | 3.02 wt % | 2.95 wt % | 2.70 wt % |
| (16) NaCl | — | 0.508 g | 1.524 g | 5.087 g |
| Wt % NaCl | — | 1.0 wt % | 3.0 wt % | 10.1 wt % |
| Firmness | 6.51N | 3.77N | 3.15N | NM2 |
| Stability Temp | 54.0° C. | 61.6° C. | 64.7° C. | NM4 |
| Po | 1.00 | 1.00 | 1.00 | 1.00 |
| Ps | 1.00 | 1.00 | 1.00 | 1.00 |

TABLE 9

| | Sample AE 1531-13 Inventive | Sample AF 1531-14 Inventive | Sample AG 1531-15 Inventive |
|---|---|---|---|
| Water | 48.0 g | 47 g | 43.6 g |
| NaM | 1.5 g | 1.5 g | 1.35 g |
| % Crystallizing Agent | 3.00 wt % | 3.00 wt % | 2.70 wt % |
| NaCl (post) | 0.5 g | 1.5 g | 5.0 g |
| Wt % NaCl | 1.0 wt % | 3.0 wt % | 10.1 wt % |
| Firmness | 8.47N | 9.31N | 9.53N |
| Stability Temp | 55.5° C. | 61.7° C. | 76.7° C. |
| Po | 1.00 | 1.00 | 1.00 |
| Ps | 1.00 | 1.00 | 1.00 |

Example 4

This example illustrates the difference between inventive samples in this specification relative to bar soap compositions, exemplified by Example AH. The example fails to meet all three performance criteria. Specifically, the thermal stability temperature of the composition is too low to effectively survive reliably on the shelf life or in the supply chain. Not wishing to be bound by theory, it is believed the chain length of 12 is far too soluble owing to the short chain length (i.e. Sample J) such that—even with a 1 wt % addition of the sodium chloride, the C12 solubilizes below 40° C.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

A solution was prepared by adding water (1), sodium chloride (16) and lauric acid (17) to the beaker. The beaker was placed on the heated mixing device. The overhead stirrer was placed in the beaker and set to rotate at 100 rpm. The heater was set and the preparation was heated to 71° C. Sodium hydroxide (15) was then added to the solution to neutralize the fatty acid and the entire mixture was heated to 95° C. The solution was then placed in cooling jars (Flak-Tech, Max 60 Cup Translucent, Cat #501 222t) and set on the bench to cool at room temperature 25 (±3° C.) until solid. Firmness measurements were made with the FIRMNESS TEST METHOD, thermal stability measurement was made by the THERMAL STABILITY TEST METHOD, water expression was made by the AQUEOUS PHASE EXPRESSION TEST METHOD and purity was determined from the BLEND TEST METHOD.

TABLE 10

| | Sample AH FG4007-1 Comparative |
|---|---|
| (1) Water | 71.500 g |
| (16) NaCl | 1.002 g |
| (17) HL | 4.506 g (22.5 mmol) |
| (15) NaOH | 22.500 g (563 mmol) |
| % Crystallizing Agent | 5.0 wt % |
| Firmness | 11.43N |
| AP Expression | 2,810 J m−3 |
| Stability Temp. | 35.5° C. |
| Po | 0.00 |
| Ps | [1.00] |

Example 5

It is understood in the examples below, the 'crystallizing agent' refer to group of crystallizing agents (4-6) and combinations, thereof.

Materials (1) Water
(4) Sodium myristate (NaC14)
(5) Sodium palmitate (NaC16)
(6) Sodium stearate (NaC18)
(19) Skin treatment active
(20) Skin-feel active
(21) Fragrances
(22) Oil based actives
(23) Optional actives In this embodiment, it is further understood in the examples below, the 'skin treatment actives' refer to actives that are design to provide treatment to skin, including but not limited to 1-menthol, frescolat MGA and other sensate, and combinations, thereof. In this embodiment, it is further understood in the examples below, the 'skin-feel actives' refer to actives that are designed to change the tactile properties of the skin, including but not limited to starch, talc, silica, ozokerite, arrowroot powder, tapioca, and combinations, thereof. In this embodiment, it is further understood in the examples below, the 'fragrances' refer to actives that are designed to impart olfactory characteristics to the product, including but not limited to neat perfume oils and perfume microcapsules, and combinations, thereof. In this embodiment, it is further understood in the examples below, the 'oil based actives' refer to actives that are oily, waxy or combinations thereof, including but not limited to oils, essential oils, mint oil, peppermint oil, coconut oil, candelilla wax, jojoba seed oil, hydrogenated castor oil, petrolatum, mineral oil, silicone oil, sunflower seed oil, citrus orange peel oil, dimethicone, C20-C40 Pareth-10, shea butter, and combinations, thereof. In this embodiment, it is further understood in the examples below, the 'optional actives' refer to actives that are not traditionally added to shave compositions but desirable for skin treatment, including but not limited to the treatment of wrinkles, treatment of dark spots, moisturization, UV protection, anti-aging, superficial scarring, treatment of pre-cancerous skin spots, exfoliating agents, chemical peels, pore moisturizers, anti-oxidants, retinol, acne treatment and treatment peptides, and combinations, thereof.

All compositions have sufficient water to hydrate the skin. All compositions have sufficient crystallizing agent to behave both to lubricate the skin and provide solid-like properties to the product. All compositions have perfume—whether as neat perfume or as perfume capsules. Sample AI is a firm composition, that may contain skin-feel active(s) such as tapioca starch to absorbs grease from the skin surface, making it feel smooth and dry. Sample AJ is a firm composition, that may contain acne treatment to medicate the skin during the shaving process. Sample AK is a firm composition, that may contain a skin treatment such a MGA sensate that provides a cool sensation after treatment. Sample AL is a firm composition, that may contain a medicated skin treatment essential oil to treat dry skin after shaving.

Sample AM is a softer composition, that may contain skin-feel active(s) such as tapioca starch to absorb grease from the skin surface, making it feel smooth and dry. Sample AN is a firm composition, that may contain acne treatment to medicate the skin during the shaving process. The medication may also contain tapioca starch to make any oily skin feel drier. Sample AO is a softer composition, that may contain a UV protection active such a TiO2 to protect the skin for the entire day, after shaving. Sample AP is a very firm composition, that may contain a medicated skin treatment for pre-cancerous skin with UV protections, coupled with small amount of sensate for freshening.

Preparation of Pre-Mix

Exemplified compositions are prepared using a heated mixing device. An overhead mixer (IKA Works Inc, Wilmington, NC, model RW20 DMZ) and a three-blade impeller design was assembled. All preparations may be heated on a heating-pad assembly (VWR, Radnor, PA, 7×7 CER Hotplate, cat. no. NO97042-690) where heating may be controlled with an accompanying probe.

The solutions may be prepared by adding water (1) and crystallizing agents (2-4) to the 250 ml stainless steel beaker (Thermo Fischer Scientific, Waltham, MA). Preferred concentrations of water will be greater than about 90 wt %, more preferably greater than about 95 wt %, most preferably greater than about 98 wt %. Preferred concentrations of crystallization agent will be less than about 10 wt %, more preferably less than about 5 wt %, most preferably greater than about 2 wt %. Such preferred compositions ensure the mixtures—once heated, are homogeneous and low viscosity, for ideal mixing.

The beaker is placed on the heated mixing device. The overhead stirrer is placed in the beaker, into the mixture and set to rotate at 100 rpm. The heater is set to about 90° C. and the preparation is heated until it forms a homogeneous, low-viscosity liquid mixture.

Addition-of-Active Agents

The step of the addition-of-active agents may vary with the type of active agents. Actives may be added in the liquid mixture at the process temperature or lower pre-cool temperature. The pre-cool temperature is between the process temperature and crystallization temperature, typically between 40° C.-60° C. At these temperatures, the crystallizing agent may begin to crystallize. but crystallization is a slow process so that additions at lower pre-cool temperature should happen quickly after several minutes before significant crystallization occurs.

A composition that comprise 'skin treat actives' and 'skin-feel actives' agent(s), these agents may be added when the mixtures is at the process temperature or at pre-cooled temperature. Preferred concentrations of these active agents maybe be less than about 3 wt %, preferably less than about 2 wt %, most preferably less than about 1 wt %, where, all weight percent are in reference to the final composition of the rheological solid composition.

A composition that comprise 'fragrances', these active agents are best added at pre-cooled temperature, because these materials are general volatile and may have a low temperature flash point. The addition of these agents often requires enhanced stirring in rate and time, to ensure proper emulsification (neat oils), and should be added last to ensure the shortest possible cooling times in the cooling-and-molding step. Preferred concentrations of fragrance(s) maybe be less than about 10 wt %, preferably less than about 5 wt %, most preferably less than about 3 wt %, where, all weight percent are in reference to the final composition of the rheological solid composition.

A composition that comprise 'oil based materials' should be added at process temperature. It is far easier to disperse liquids—such as waxes and oils above their melt point temperature. Preferred concentrations of perfume microcapsules maybe be less than about 5 wt %, preferably less than about 3 wt %, most preferably less than about 1 wt %, where, all weight percent are in reference to the final composition of the rheological solid composition.

A composition that comprise 'optional actives' may be added when the mixtures is at the process temperature or at pre-cooled temperature. These actives contain a wide range of materials, and each material must be assessed independent about chemical and physical stability at different temperatures. Preferred concentrations of optical brighteners maybe be less than about 2 wt %, preferably less than about 1 wt %, most preferably less than about 0.5 wt %, where, all weight percent are in reference to the final composition of the rheological solid composition.

Cooling-and-Molding

The mixtures after the addition-of-active agent step is converted into a rheological solid composition.

One suitable approach is to mold the mixture into regular shapes. Preferred shapes include sticks, sheets, beads, balls, gummy bears, razor attachment, strip on a razor and along of other consumer preferred shapes. The liquid mixture should be placed in these molds and the molds keep quiescent at the crystallization temperature, until the mixture completely crystallizes.

The consumer product may be use with a shave implement or part of shave implement. Optionally, the composition may be used in a stick form and applied to a man's face over whiskers. It may be allowed to rest on this area for ten to fifteen seconds, when a razor can be used to remove the whiskers. Optionally, the composition may be used in a stick form applied to a woman's legs over the area desired to remove hair. It may be allowed to rest on this area for ten to fifteen seconds, when a razor can be used to remove the undesired hair. Optionally, the composition may be part of an assembled product, where the rheological solid composition is affixed to a hair removal device such as a razor, and used simultaneously in the shave process. Optionally, the composition can be used independent of a shave implement, to hydrate and/or treat the skin.

TABLE 11

| | Example AI Inventive | Example AJ Inventive | Example AK Inventive | Example AL Inventive |
|---|---|---|---|---|
| (1) Water | 91.0 g | 91.0 g | 91.0 g | 93.0 g |
| (4) NaC14 | 5.0 g | 5.0 g | 5.0 g | 5.0 g |
| (5) NaC16 | — | — | — | — |
| (6) NaC18 | — | — | — | — |
| (19) Skin treatment active | — | — | 2.0 g | — |
| (20) Skin-feel active | 2.0 g | — | — | — |
| (21) Fragrances | 2.0 g | 2.0 g | 2.0 g | 1.0 g |
| (22) Oily actives | — | — | — | 1.0 g |
| (23) Optional actives | — | 2.0 g | — | — |

TABLE 12

| | Example AM Inventive | Example AN Inventive | Example AO Inventive | Example AP Inventive |
|---|---|---|---|---|
| (1) Water | 93.0 g | 90.0 g | 89.5 g | 88.0 g |
| (4) NaC14 | 3.0 g | 5.0 g | — | 7.0 g |
| (5) NaC16 | — | — | 5.0 g | — |
| (6) NaC18 | — | — | 1.0 g | — |
| (19) Skin treatment active | — | 2.0 g | — | 1.0 g |
| (20) Skin-feel active | 2.0 g | — | — | — |
| (21) Fragrances | 2.0 g | 1.0 g | 2.5 g | — |
| (22) Oily actives | — | — | — | — |
| (23) Optional actives | — | 2.0 g | 2.0 g | 4.0 g |

Shave Compositions

Tables 13 and 14 include shave compositions of the present invention. These compositions are made via the general processes outlined above and generally involve mixing and heating the compositions followed by cooling and forming the rheological solid. Components may be added individually or pre-mixes may be used to help facilitate the dissolution and/or suspension of ingredients.

Suspension Agent Pre-Mix

Where a suspension agent is used, the suspension agent may be pre-mixed in one of the other ingredients to facilitate its distribution and dissolution in the composition. For example, the xanthan—may be pre-suspended or dissolved in the aqueous phase or in glycerol.

Oily Compositions

Oil/Petrolatum pre-mixtures may also be useful in the present invention. For example, the petrolatum and/or other oily components may be mixed and heated, such as to approximately 50-60° C. to liquify the petrolatum prior to compounding the composition.

Crystalizing Agent Pre-Mix

Crystallizing agents may be pre-suspended/dissolved in the aqueous phase, or a portion of the aqueous phase, prior to compounding the composition. The crystallizing agent pre-mix may further include the salt, such as sodium chloride.

Rheological solid shave compositions of the present invention are given in table 13 and 14.

TABLE 13

| | Post-Shave Compositions | | | | | | | | | |
|---|---|---|---|---|---|---|---|---|---|---|
| Example # | 1 | 2 | 3 | 4 | 5 | 6 | 7 | 8 | 9 | 10 |
| Water | 89 | 79 | 67.4 | 59.7 | 88.7 | 92.25 | 92.6 | 91.7 | 86.6 | 80.6 |
| Sodium Myristate | 5 | 5 | | | | 5 | 5 | 5 | 5 | 5 |
| Sodium Palmitate | | | 5 | 5 | 5 | | | | | |
| Sodium chloride | 1 | 1 | 1 | 3.5 | 3.5 | 1 | 1 | 1 | 1 | 1 |
| Xanthan Gum | | | 0.3 | 0.3 | 0.3 | | 0.3 | 0.3 | 0.3 | 0.3 |
| Tospearl CF600 (1) | 4 | 4 | | | | | | | | |
| Glycerine | | 10 | 5 | 5 | | | | | | |
| Panthenol | | | 1 | 1 | | | | | | 1 |
| Petrolatum | | | 5 | 12.5 | | | | | | 5 |
| Mineral Oil | | | 15 | 12.5 | | | | | | 5 |
| Salsphere (2) | | | | | 1.5 | | | | | |
| G180 (3) | | | | | | 0.05 | | | | |
| Menthol | | | | | | 0.2 | | | | |
| Menthone Glycerin Acetal | | | | | | 0.5 | | | | |
| ZPT | | | | | | | 0.1 | | | |
| Zinc Oxide | | | | | | | | 1 | | |
| PMX-1503 (7) | | | | | | | | | 1 | |
| PDMS 100 cst | | | | | | | | | 5 | |
| Fragrance | | | 0.1 | 0.3 | | | | | | 1 |
| Phenoxyethanol | 0.4 | 0.4 | | | 0.4 | 0.4 | 0.4 | 0.4 | 0.4 | 0.4 |
| Euxyl PE 9010 (10) | | | 0.1 | 0.1 | | | | | | |
| Symdiol 68 (11) | 0.6 | 0.6 | | | 0.6 | 0.6 | 0.6 | 0.6 | 0.6 | 0.6 |
| BHT | | | 0.1 | 0.1 | | | | | 0.1 | 0.1 |

TABLE 14

| | Pre-Shave Compositions | | | | | |
|---|---|---|---|---|---|---|
| Example # | 11 | 12 | 13 | 14 | 15 | 16 |
| Water | 87.5 | 88 | 93 | 92 | 92 | 84.5 |
| Sodium Myristate | 5 | 5 | 5 | 5 | 5 | 5 |
| Sodium chloride | 0.5 | 0.5 | 0.5 | 0.5 | 0.5 | 0.5 |
| Xanthan Gum | | | | | 0.3 | |
| Glycerine | | 5 | | | | |
| Sorbitol | 5 | | | | | 5 |
| Polyox 301 (4) | 0.5 | | | 0.5 | 0.5 | 0.5 |
| Cekol 30000 (5) | | 0.5 | | | | |
| Methocel K100M (6) | | | 0.5 | | | |
| Pluronic F127 (8) | | | | 0.5 | | |
| Silsoft 405 (9) | | | | | 0.2 | |
| SLES | | | | | | 2 |
| Fragrance | | | | | | 1 |
| Phenoxyethanol | 0.4 | 0.4 | 0.4 | 0.4 | 0.4 | 0.4 |

TABLE 14-continued

| Pre-Shave Compositions | | | | | | |
|---|---|---|---|---|---|---|
| Example # | 11 | 12 | 13 | 14 | 15 | 16 |
| Symdiol 68 (11) | 0.6 | 0.6 | 0.6 | 0.6 | 0.6 | 0.6 |
| BHT | | | | 0.5 | | |
| Ralox 35 (12) | 0.5 | | | | 0.5 | 0.5 |

(1) Polymethylsilsesquioxane available from Momentive (2) Encapsulated salicylic acid available from Salvona (3) N-[4-(cyanomethyl)phenyl]-5-methyl-2-propan-2-yl-cyclohexane-1-carboxamide available from Givaudan (4) Polyethylene oxide available from Dow (5) Sodium Carboxymethylcellulose available from CP Kelco Not wishing to be bound by theory, it is believed that the basic unit operations described can be scaled with the size of the batch. Therefore, it is expected that the same making process described can apply to commercial scale batches. Further, while described as a batch process, it is expected such compositions may be prepared also in a continuous process. It further follows that the order of addition of components into the batch process is non-limiting.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rheological solid shave care composition in the form of a stick comprising:

a. a crystallizing agent comprising a blend of sodium myristate, sodium palmitate, and sodium stearate, wherein the crystallizing agent blend has an Optimal Purity (Po) of greater than about 0.3 and a Single Purity (Ps) of greater than about 0.5;

b. an active;

c. an aqueous phase; and wherein the amount of crystallizing agent in the composition is between 0.5 wt. % and 10 wt. %;

wherein the composition further comprises a suspension agent, wherein the suspension agent consists of xanthan gum and konjac gum;

wherein the composition has a firmness from about 5.0 N to about 10.0 N.

2. The rheological solid shave care composition of claim 1, wherein the active comprises at least one of an insoluble active or soluble active.

3. The rheological solid shave care composition of claim 2, wherein the active comprises at least one of: oil control actives, mattifying powders, acne actives, moisturizers, silicones, oils, anti-irritation and redness actives, fragrances, sensates, encapsulated actives, anti-bacterial actives, and lubricants.

4. The rheological solid shave care composition of claim 2, wherein the active comprises an insoluble active particle comprising an insoluble oil.

5. The rheological solid shave care composition of claim 1, wherein the rheological solid shave care composition further comprises a hydrophobic non-aqueous vehicle.

6. The rheological solid shave care composition of claim 1, wherein the suspension agent is present in an amount from about 0.01 to about 2 wt. %, by weight of the rheological solid shave care composition, and the active is present in amount from about 0.1 to about 30 wt. %, by weight of the rheological solid shave care composition.

7. The rheological solid shave care composition of claim 1, wherein the composition is incorporated into an implement.

8. The rheological solid shave care composition of claim 7, wherein the implement is an applicator or stick dispenser.

* * * * *